United States Patent
Yoon et al.

(10) Patent No.: US 9,705,086 B2
(45) Date of Patent: Jul. 11, 2017

(54) BLUE FLUORESCENT COMPOUNDS AND ORGANIC LIGHT EMITTING DIODE DEVICES USING THE SAME

(71) Applicant: LG DISPLAY CO., LTD., Seoul (KR)

(72) Inventors: Daewi Yoon, Paju-si (KR); Soonwook Cha, Goyang-si (KR); Kyunghoon Lee, Seoul (KR); Seogshin Kang, Goyang-si (KR); Kyungjin Yoon, Goyang-si (KR); Suyeon Lee, Paju-si (KR); Hyojin Noh, Paju-si (KR)

(73) Assignee: LG DISPLAY CO., LTD., Seoul (KR)

( * ) Notice: Subject to any disclaimer, the term of this patent is extended or adjusted under 35 U.S.C. 154(b) by 725 days.

(21) Appl. No.: 14/108,664

(22) Filed: Dec. 17, 2013

(65) Prior Publication Data
US 2014/0183485 A1    Jul. 3, 2014

(30) Foreign Application Priority Data

Dec. 27, 2012 (KR) .................. 10-2012-0155185

(51) Int. Cl.
*H01L 51/50* (2006.01)
*C07C 11/06* (2006.01)
(Continued)

(52) U.S. Cl.
CPC .......... *H01L 51/0058* (2013.01); *C07C 15/28* (2013.01); *C07D 307/91* (2013.01);
(Continued)

(58) Field of Classification Search
CPC ................................... C07C 15/28
See application file for complete search history.

(56) References Cited

U.S. PATENT DOCUMENTS

| 9,428,407 B2* | 8/2016 | Yue | C02F 1/288 |
| 2008/0100207 A1* | 5/2008 | Park | C07C 13/62 |
| | | | 313/504 |
| 2009/0288707 A1* | 11/2009 | Lee | C07D 403/04 |
| | | | 136/257 |

FOREIGN PATENT DOCUMENTS

| CN | 1844302 A | 10/2006 |
| JP | 2008294184 A | 12/2008 |
| WO | WO 2009/154207 A1 | 12/2009 |

OTHER PUBLICATIONS

English Translation of JP2008294184, Retrieved Jul. 14, 2016, Japanese Published Dec. 4, 2008.*

(Continued)

*Primary Examiner* — Francisco Tschen
(74) *Attorney, Agent, or Firm* — Brinks Gilson & Lione

(57) ABSTRACT

A blue fluorescent compound is disclosed. The blue fluorescent compound represented by the following Chemical Formula 1,

[Chemical Formula 1]

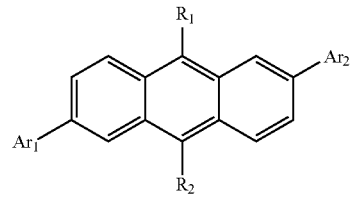

where $R_1$ and $R_2$ are each independently selected from the group consisting of C0-C18 saturated hydrocarbon carbons, branched saturated hydrocarbons, and saturated ring hydrocarbons, and $Ar_1$ and $Ar_2$ are each independently selected (Continued)

from the group consisting of C1-C20 aromatic compounds, heteroaromatic compounds, C1-C18 saturated hydrocarbons, C1-C18 branched saturated hydrocarbons, and C1-C18 saturated ring hydrocarbons.

10 Claims, 4 Drawing Sheets

(51) Int. Cl.
    *H01L 51/00*    (2006.01)
    *C07D 333/76*   (2006.01)
    *C07D 307/91*   (2006.01)
    *C07C 15/28*    (2006.01)
    *C09K 11/06*    (2006.01)

(52) U.S. Cl.
    CPC ............ *C07D 333/76* (2013.01); *C09K 11/06* (2013.01); *H01L 51/0052* (2013.01); *H01L 51/0074* (2013.01); *C07C 2103/24* (2013.01); *C09K 2211/1011* (2013.01); *C09K 2211/1092* (2013.01); *H01L 51/0073* (2013.01); *H01L 51/50* (2013.01); *H01L 51/5012* (2013.01)

(56) References Cited

OTHER PUBLICATIONS

Ito et al., Oligo(2,6-anthrylene)s: Acene—Oligomer Approach for Organic Field-Effect Transistors, Angew. Chem. 2003, 115, Nr. 10, 1191-1194.*
Office Action issued in Chinese Patent Application No. 201310298274.9, mailed Jan. 26, 2015, 12 pages.

* cited by examiner

BLUE FLUORESCENT COMPOUNDS AND ORGANIC LIGHT EMITTING DIODE DEVICES USING THE SAME

This application claims the benefit of priority to Korean Patent Application No. 10-2012-0155185 filed on Dec. 27, 2012, which is incorporated herein by reference for all purposes as if fully set forth herein.

BACKGROUND

Field of the Disclosure

This disclosure relates to blue fluorescent compounds and organic light emitting devices using the same, and more particularly, to organic light emitting diode devices using blue fluorescent compounds, which make solution processing easy, as the host of an emission layer.

Discussion of the Related Art

With the development of multimedia, flat panel displays (FDPs) are becoming more and more important. Accordingly, a variety of flat panel displays such as liquid crystal display (LCDs), plasma display panels (PDPs), field emission displays (FEDs), organic light emitting diode devices, and the like are put to practical use.

Among them, an organic light emitting diode device can be formed on a flexible transparent substrate, such as plastic, can be driven at a lower voltage (below 10V) than a plasma display panel or inorganic light emitting diode display, has relatively low power consumption, and has a superior color sense. Further, the organic light emitting diode device can represent three colors of green, blue and red, and thus is drawing a great deal of attention as a next-generation full-color display device.

The organic light emitting diode device can be formed by sequentially laminating an anode, a hole injection layer, a hole transport layer, an emission layer, and electron transport layer, an electron injection layer, and a cathode. For a light-emitting material, holes injected from the anode are recombined with electrons injected from the cathode to form excitons. Singlet excitons and triplet excitons are involved in the fluorescence and phosphorescence processes, respectively. The light-emitting material may be formed by deposition or a solution process.

In the solution process, light emitting compounds are easy to prepare, but they have very low solubility in an organic solvent. That is, the host material of the emission layer is mostly made of aromatic hydrocarbon and thus has very low solubility in an organic solvent. Moreover, the efficiency and life-span of devices fabricated using the solution process are much poorer than those of devices fabricated using the deposition process. This creates the need for the development of novel solution-type host materials.

SUMMARY

In one aspect, there is a blue fluorescent compound represented by the following Chemical Formula 1,

[Chemical Formula 1]

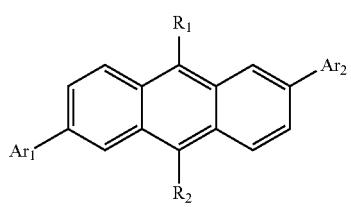

where $R_1$ and $R_2$ are each independently selected from the group consisting of C0-C18 saturated hydrocarbon carbons, branched saturated hydrocarbons, and saturated ring hydrocarbons, and $Ar_1$ and $Ar_2$ are each independently selected from the group consisting of C1-C20 aromatic compounds, heteroaromatic compounds, C1-C18 saturated hydrocarbons, C1-C18 branched saturated hydrocarbons, and C1-C18 saturated ring hydrocarbons.

In another aspect, there is an organic light emitting diode device comprising an organic film formed between an anode and a cathode, the organic film comprising the blue fluorescent compound.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE EMBODIMENTS

Reference will now be made in detail to embodiments of the invention, examples of which are illustrated in the accompanying drawings. Wherever possible, the same reference numbers will be used throughout the drawings to refer to the same or like parts. It will be paid attention that detailed description of known arts will be omitted if it is determined that the arts can mislead the embodiments of the invention.

Figure 1:
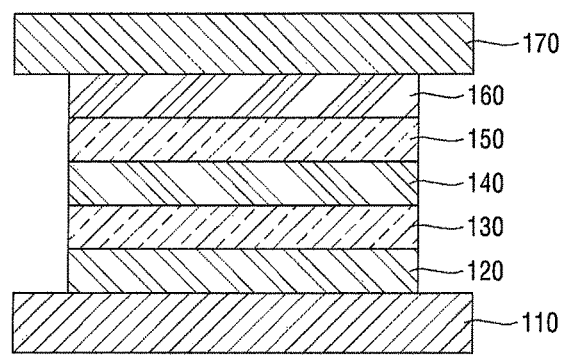
FIG. 1 is a view showing an organic light emitting diode device in accordance with an exemplary embodiment of the present invention.

FIG. 1 is a view showing an organic light emitting diode device in accordance with an exemplary embodiment of the present invention.

Referring to FIG. 1, the organic light emitting diode device 100 in accordance with the exemplary embodiment of the present invention may comprise an anode 110, a hole injection layer 120, a hole transport layer 130, an emission layer 140, an electron transport layer 150, an electron injection layer 160, and a cathode 170.

The anode 110 is a hole injection electrode which is formed of one of ITO (Indium Tin Oxide), IZO (Indium Zinc Oxide), and ZnO (Zinc Oxide) having a high work function. If the anode 110 is a reflective electrode, the anode 110 may further comprise a reflective layer formed of one of aluminum (Al), silver (Ag), or nickel (Ni) under the layer formed of one of ITO, IZO, and ZnO.

The hole injection layer 120 functions to facilitate the injection of holes from the anode 110 to the emission layer 140. The hole injection layer 120 may be formed of at least one selected from the group consisting of copper phthalocyanine (CuPc), PEDOT (poly(3,4)-ethylenedioxythiophene), polyaniline (PANI), and NPD (N,N-dinaphthyl-N, N'-diphenyl benzidine), but is not limited thereto.

The thickness of the hole injection layer 120 may range from 1 to 150 nm. If the thickness of the hole injection layer 120 is 1 nm or greater, a reduction in a hole injection characteristic can be prevented. If the thickness of the hole injection layer 120 is 150 nm or less, an increase in driving voltage, which is applied in order to increase the movement of holes when the thickness of the hole injection layer 120 is too large, can be prevented.

The hole transport layer 130 functions to smoothly transport holes. The hole transport layer 130 may be formed of at least one selected from the group consisting of NPD (N,N-dinaphthyl-N,N'-diphenyl benzidine), TPD (N,N'-bis-(3-methylphenyl)-N,N'-bis-(phenyl)-benzidine, s-TAD and MTDATA (4,4',4"-Tris(N-3-methylphenyl-N-phenyl-amino)-triphenylamine), but is not limited thereto.

The hole transport layer 130 may also have a thickness of 1 to 150 nm. If the thickness of the hole transport layer 130 is 5 nm or more, a reduction in a hole transport characteristic can be prevented. If the thickness of the hole transport layer 130 is 150 nm or less, an increase in the driving voltage, which is applied in order to increase the movement of holes when the thickness of the hole transport layer 130 is too large, can be prevented.

The emission layer 140 may be made of a material that emits red, green, and blue color light. This material may comprise a phosphorescent or fluorescent material. This exemplary embodiment will be described with respect to fluorescent materials that emit blue light.

A blue fluorescent compound in accordance with an exemplary embodiment of the present invention is represented by the following Chemical Formula 1:

[Chemical Formula 1]

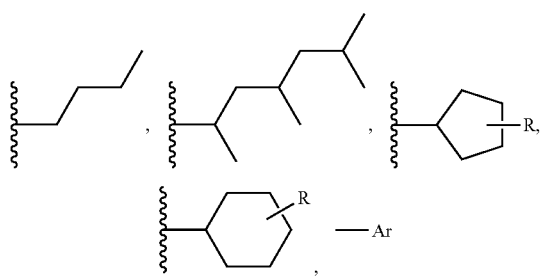

where R1 and R2 are each independently selected from the group consisting of C0-C18 saturated hydrocarbon carbons, branched saturated hydrocarbons, and saturated ring hydrocarbons, and Ar1 and Ar2 are each independently selected from the group consisting of C1-C20 aromatic compounds, heteroaromatic compounds, C1-C18 saturated hydrocarbons, C1-C18 branched saturated hydrocarbons, and C1-C18 saturated ring hydrocarbons.

R1 and R2 are each independently selected from substituents represented by R:

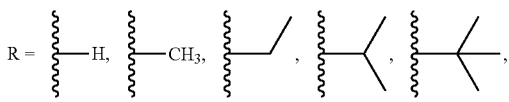

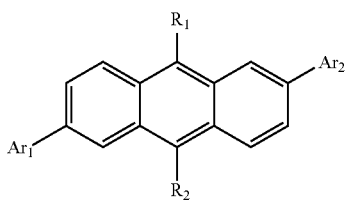

where Ar1 and Ar2 are each independently selected from substituents represented by Ar:

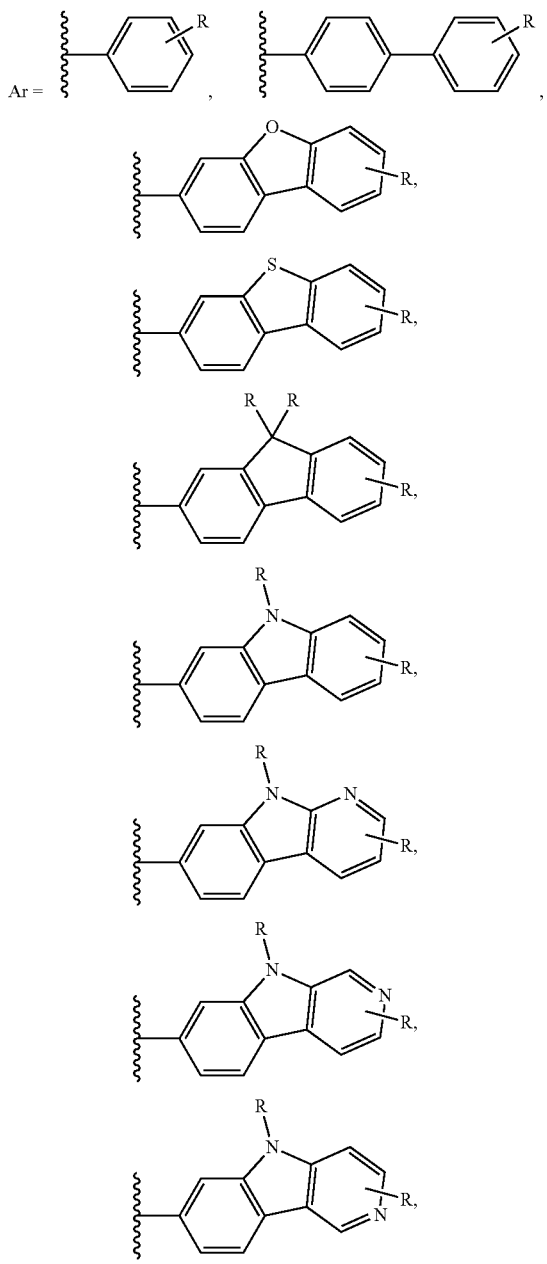

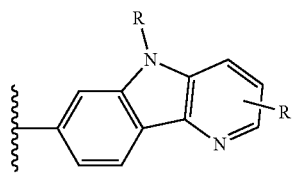
The blue fluorescent compound may be any one selected from the compounds represented below:
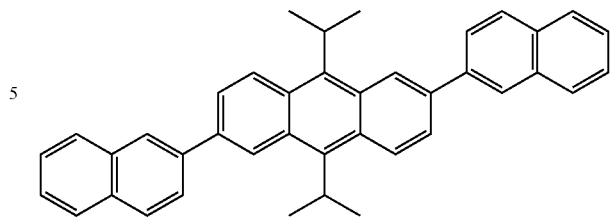
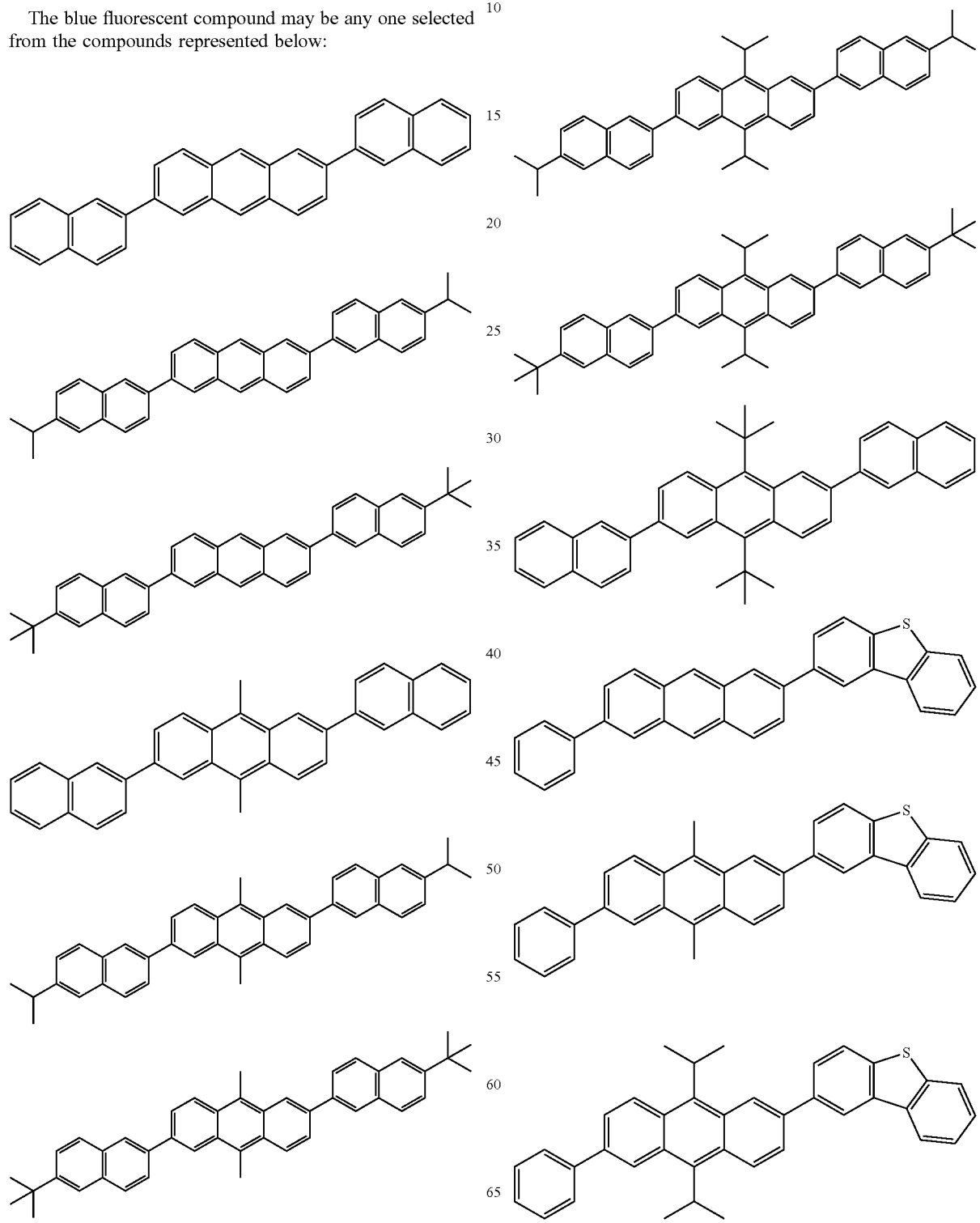

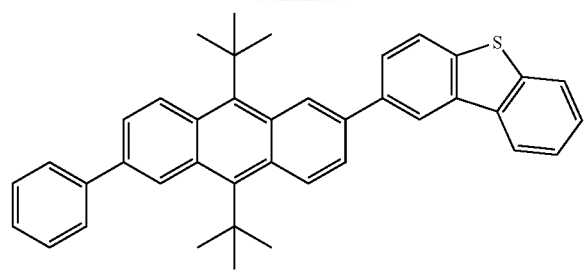
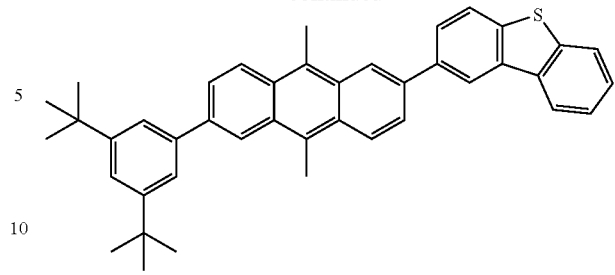

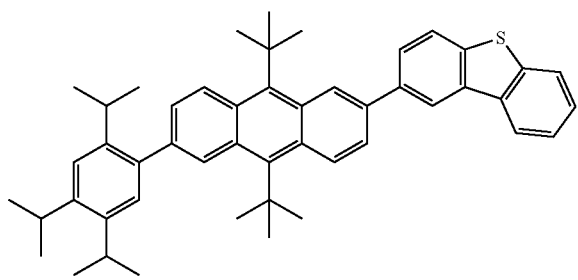
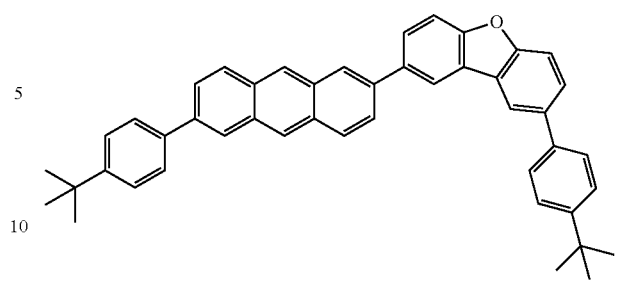
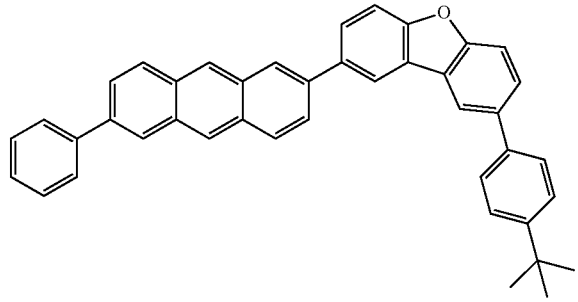
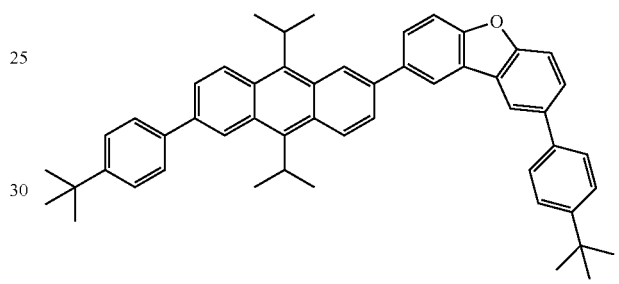
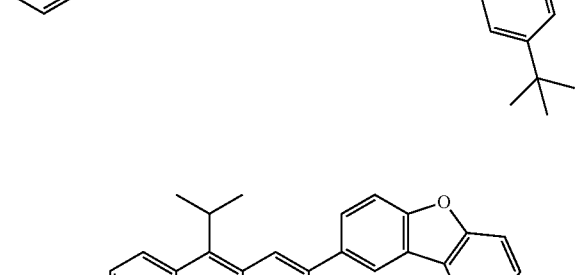
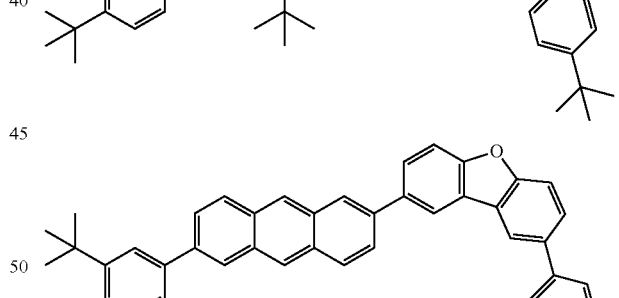
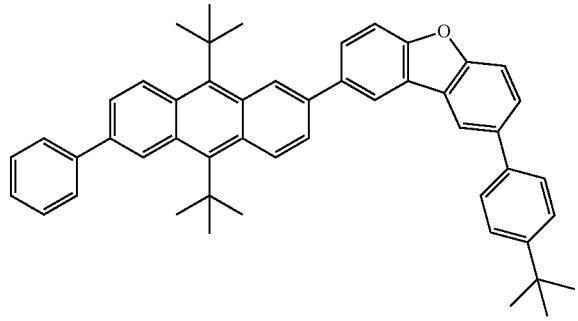
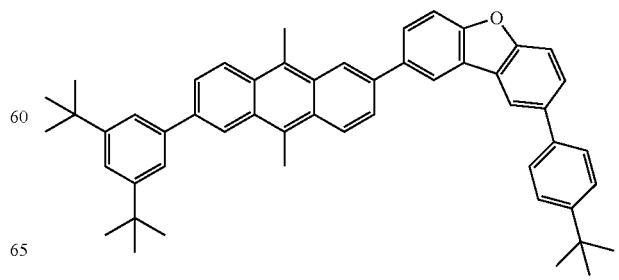

-continued
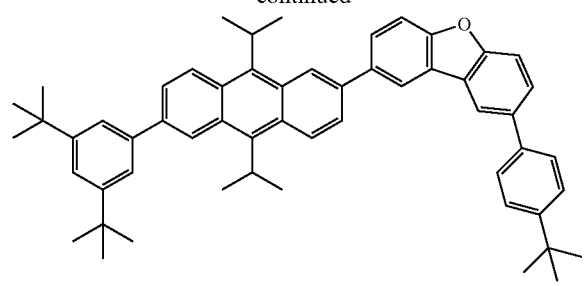
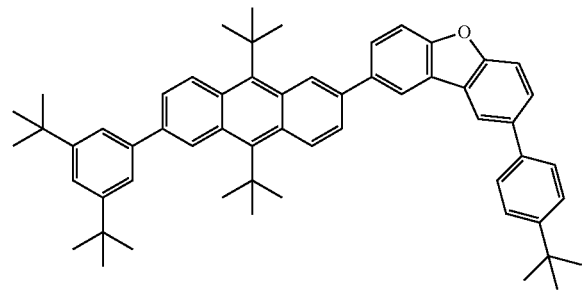
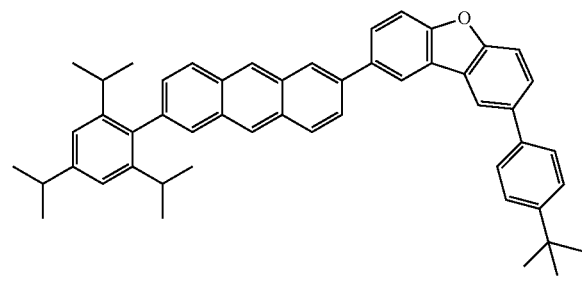
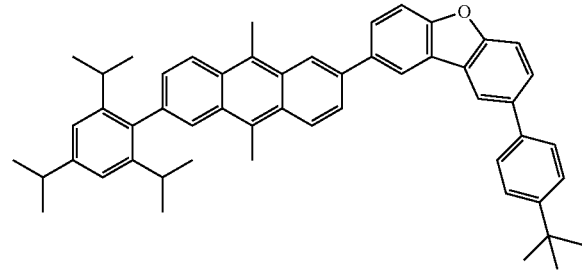
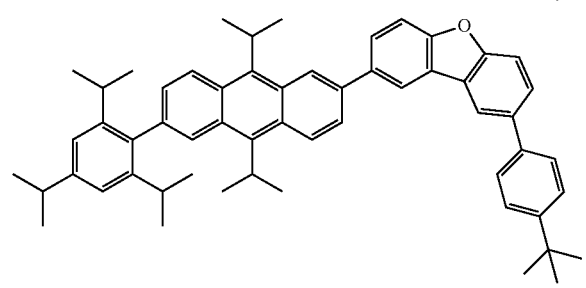
-continued
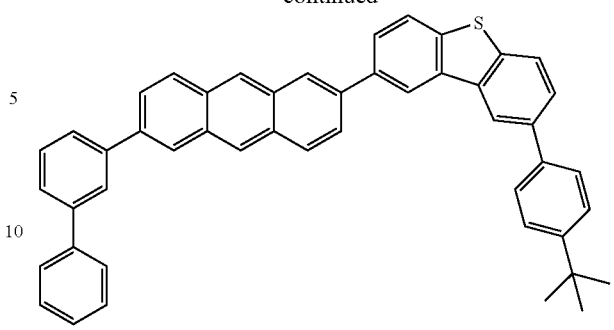
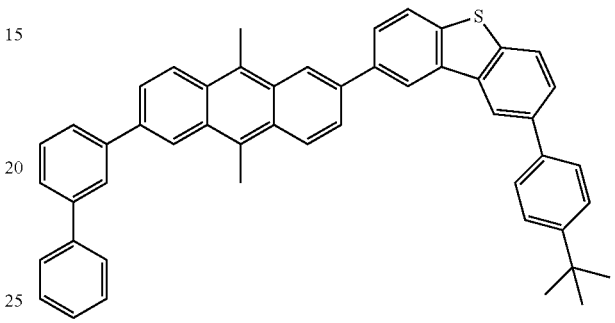
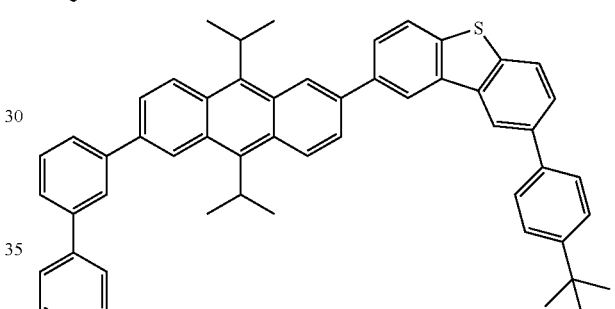
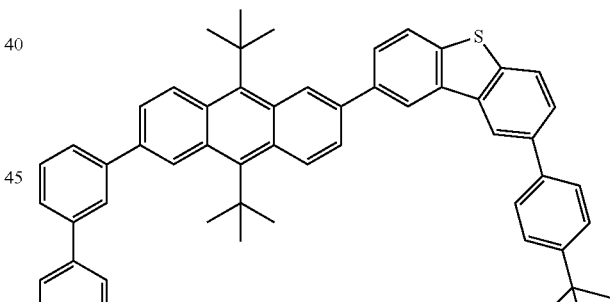
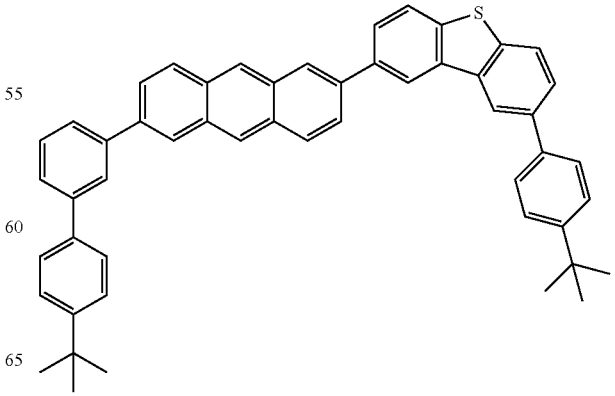

-continued
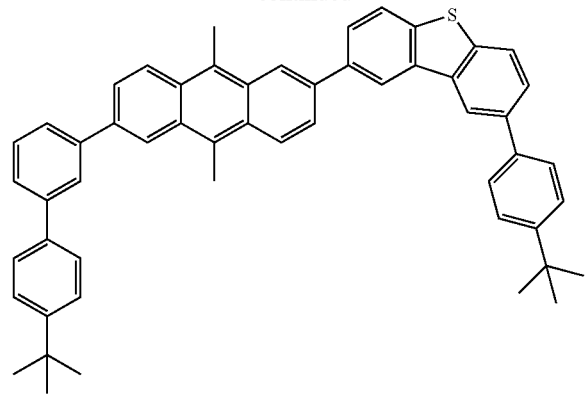
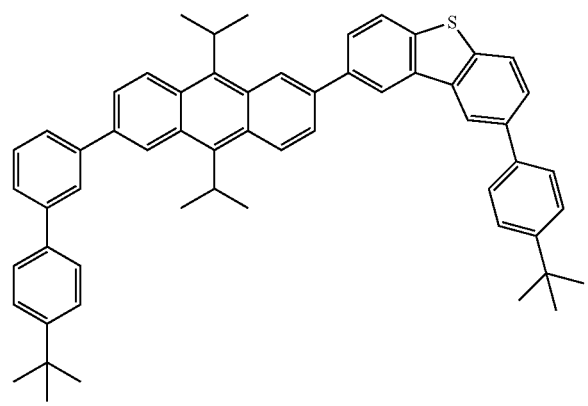
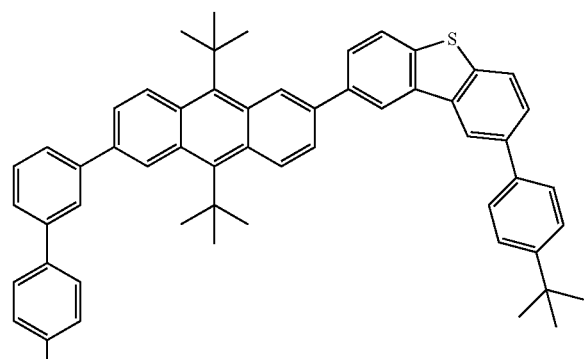
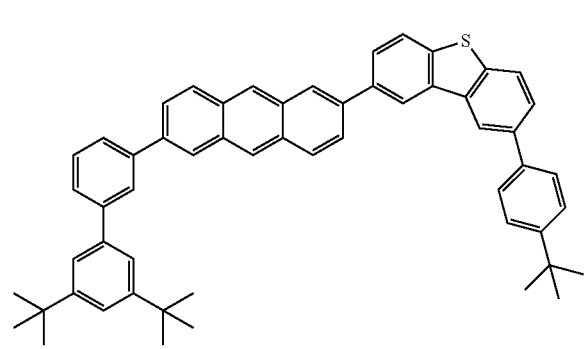
-continued
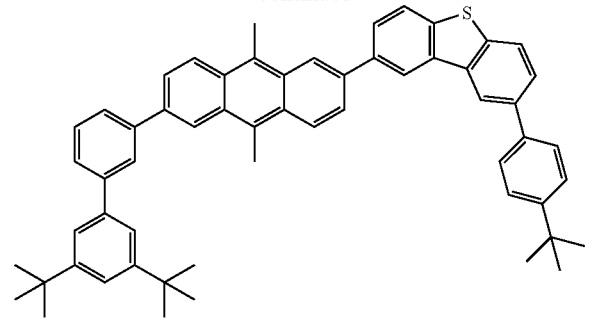
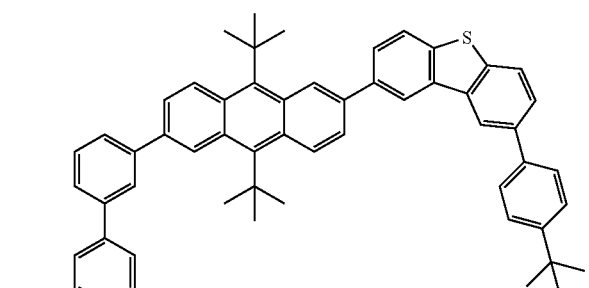
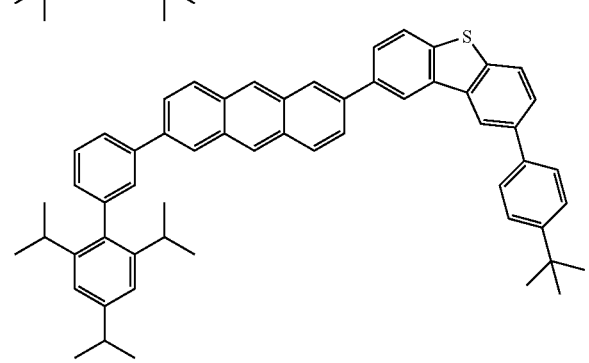
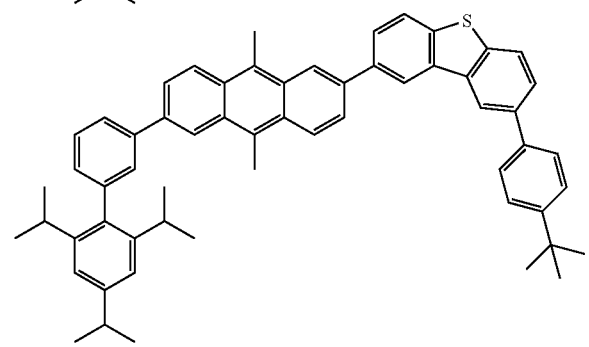

-continued

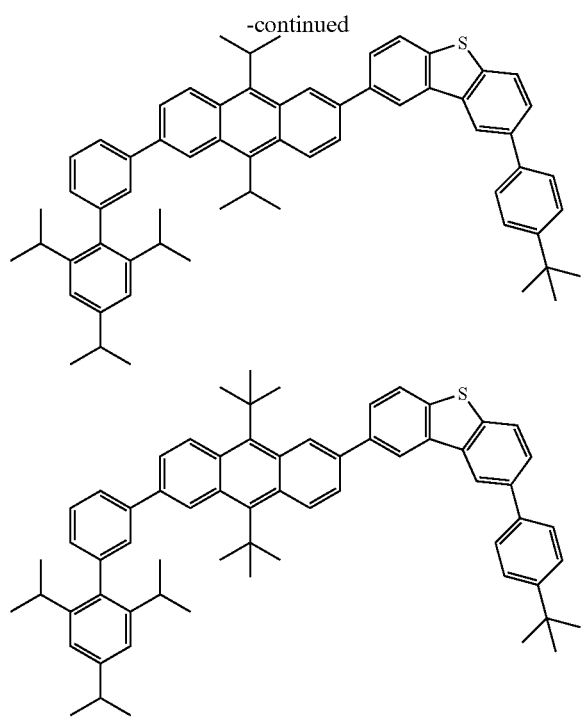

The blue fluorescent compound may be used as the host or dopant of the emission layer 140, or only the blue fluorescent compound may constitute a single emission layer without the host and dopant.

Figure 2:
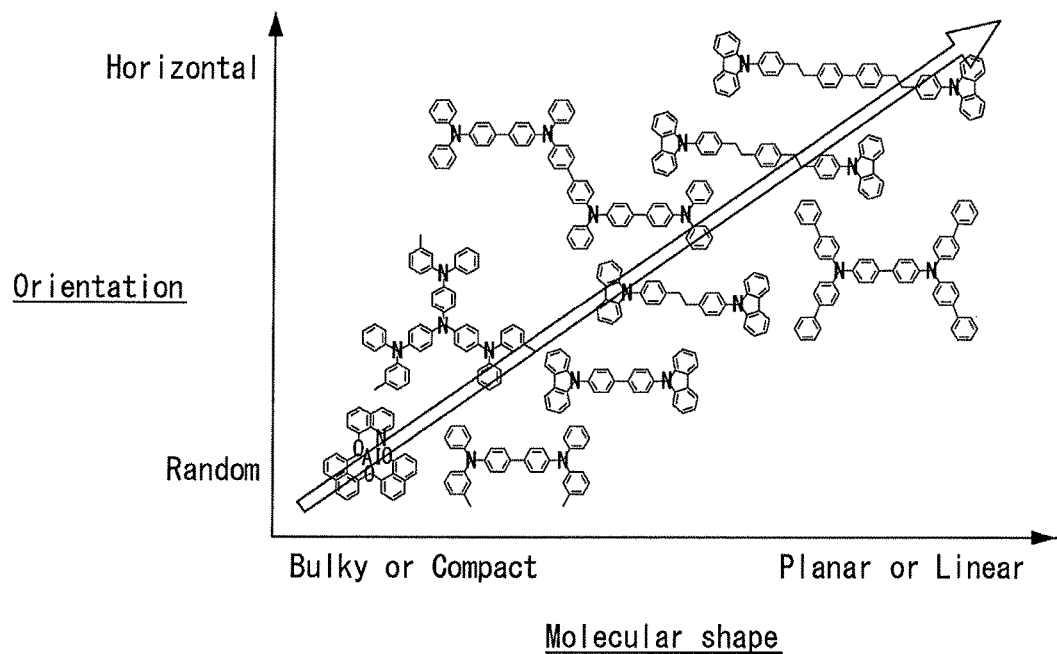
FIG. 2 is a view showing the correlation between the geometrical pattern of the molecular structure of organic compounds and the orientation of the compounds in a thin film formed by vacuum deposition.
Figure 3:
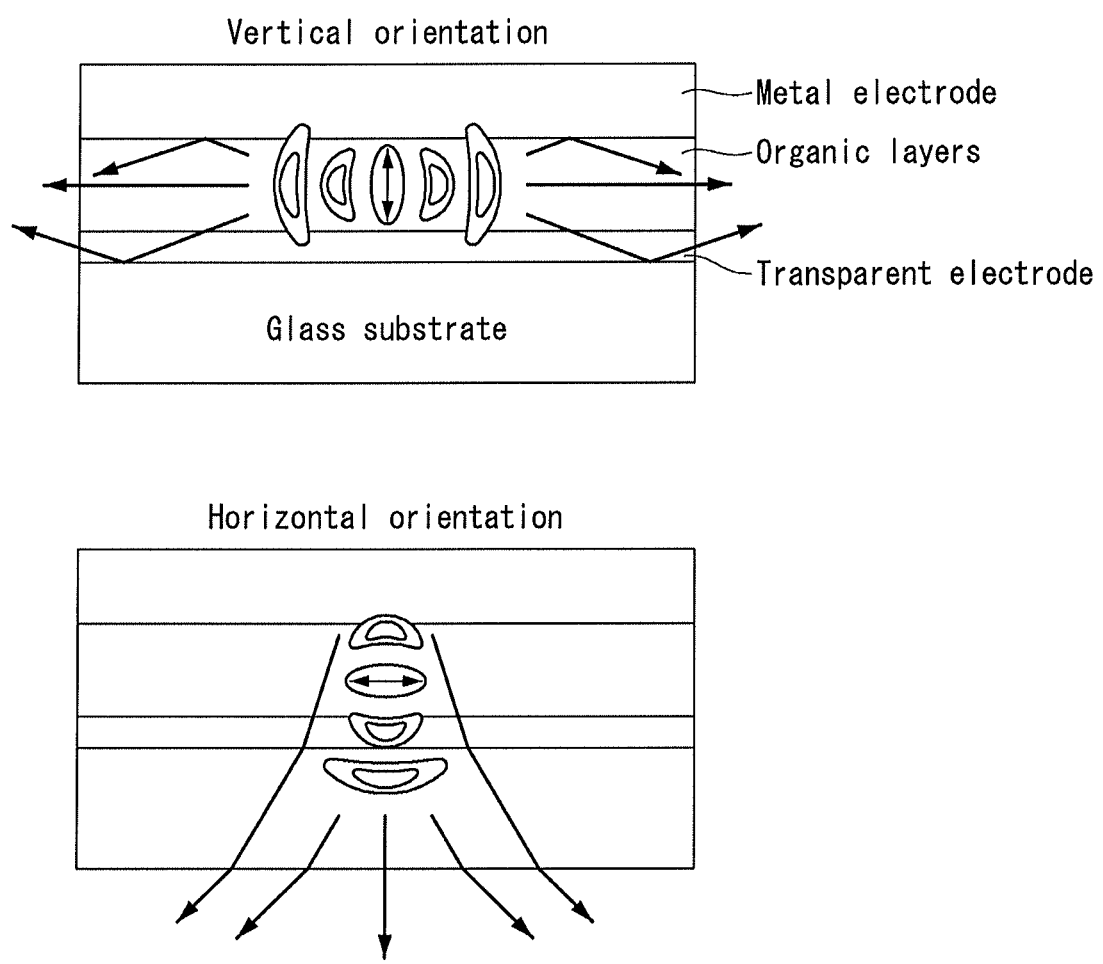
FIG. 3 is a view showing the outcoupling efficiency versus the orientation of organic compounds.

FIG. 2 is a view showing the correlation between the geometrical pattern of the molecular structure of organic compounds and the orientation of the compounds in a thin film formed by vacuum deposition. FIG. 3 is a view showing the outcoupling efficiency versus the orientation of organic compounds.

Referring to FIG. 2, if the organic compounds have a linear or planar structure, the thin film formed in the vacuum deposition process has horizontal orientation. As the linear or planar structure becomes less evident in the molecules, the orientation of the organic compounds in the thin film becomes more random. By adjusting the orientation of the emission layer to be horizontal, the outcoupling efficiency of devices is improved, as shown in FIG. 3, thereby improving the device efficiency. In FIG. 3, the outcoupling efficiency increase when the organic compounds of the emission layer maintain their horizontal orientation, because light from organic molecules is generated in a direction perpendicular to the transition dipole moment.

Accordingly, the blue fluorescent compound of the present invention increases solubility in an organic solvent by substituting the 9 and 10 positions of anthracene with saturated hydrocarbons such as methyl, iso-propyl, tert-butyl, n-butyl, iso-pentyl, and acetyl-TMS, and substituting aromatic rings at the 2 and 7 positions of anthracene with the aforementioned saturated hydrocarbons. Moreover, a linear molecular structure is designed by introducing an aromatic ring to the 2 and 7 positions of an anthracene-based core, and electron mobility is improved by introducing a dibenzothiophene, dibenzofuran, carbazole, and carboline derivatives replaced by a hetero ring to one aromatic ring, which makes it possible to adjust the charge balance in the emission layer. Further, the dipole moment of the molecules is increased by introducing a hetero aromatic ring in only one direction of the aforementioned anthracene, thereby inducing the thin film formed in the solution process to have horizontal orientation. Accordingly, the blue fluorescent compound can be designed in a long, linear planar structure to improve outcoupling efficiency.

The dopant mixed with the host of the emission layer 140 of the present invention may be in the range of 0.1 to 50 parts by weight based on 100 parts by weight of the total amount of the host.

The hole transport layer 150 functions to smoothly transport holes. The hole transport layer 150 may be formed of at least one selected from the group consisting of Alq3(tris(8-hydroxyquinolino)aluminum, PBD, TAZ, spiro-PBD, BAlq, and SAlq, but is not limited thereto.

The hole transport layer 150 may also have a thickness of 1 to 50 nm. If the thickness of the hole transport layer 150 is 1 nm or greater, a reduction in a hole transport characteristic can be prevented. If the thickness of the hole transport layer 150 is 50 nm or less, an increase in the driving voltage, which is applied in order to increase movement of holes when the thickness of the hole transport layer 150 is too large, can be prevented.

The electron injection layer 160 functions to facilitate the injection of electrons. The electron injection layer 160 may be formed of Alq3(tris(8-hydroxyquinolino)aluminum), PBD, TAZ, spiro-PBD, BAlq or SAlq, but is not limited thereto.

The thickness of the hole injection layer 160 may range from about 1 to about 50 nm. If the thickness of the hole injection layer 160 is 1 nm or greater, a reduction in a hole injection characteristic can be prevented. If the thickness of the hole injection layer 160 is 50 nm or less, an increase in driving voltage, which is applied in order to increase the movement of holes when the thickness of the hole injection layer 160 is too large, can be prevented.

The cathode 170 is an electron injection electrode which is formed of magnesium (Mg), calcium (Ca), aluminum (Al), and silver (Ag) having a low work function, or an alloy thereof. In the case that the organic light emitting diode device has a top emission or dual emission structure, the cathode 170 may be formed thin enough to transmit light. In the case that the organic light emitting diode device has a bottom emission structure, the cathode 170 may be formed thick enough to reflect light.

Hereinafter, blue phosphorescent compounds of the present invention and the properties of these compounds will be described in detail in the following Synthesis Examples. However, it should be noted that the following Synthesis Examples are merely illustrative of the present invention, and the present invention is not limited thereto.

Synthesis Examples

1) Synthesis of 2,6-dibromoanthraquinone

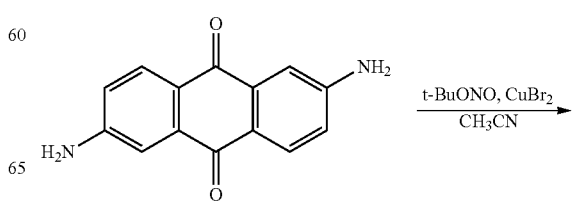

-continued

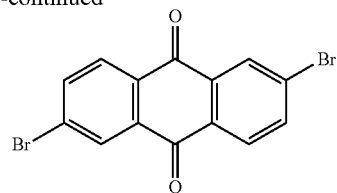

Tert-butyl nitrite (7.7 mL, 64.74 mmol) and CuBr2 (11.8025 g, 52.84 mmol) were dissolved in CH3CN (300 mL) and heated at 65☐, and 2,6-diaminoanthraquinone (5.300 g, 22.25 mmol) was gradually added to the mixture. After the generation of nitrogen gas has stopped, the mixture was maintained at 65☐ for one more hour, and then the reaction mixture was cooled at room temperature. A 3N HCl aqueous solution (250 mL) was added to the reaction mixture, and stirred at room temperature for 2 hours. The resulting precipitate was filtered under vacuum, and then the obtained solid compound was sequentially washed with an excessive amount of water, MeOH, and acetone. The solid precipitate was dried in vacuum, giving 2,6-dibromoanthraquinone (7.5743 g, 20.69 mmol, 93%).

2) Synthesis of 2,6-bis(2-naphtyl)anthraquinone

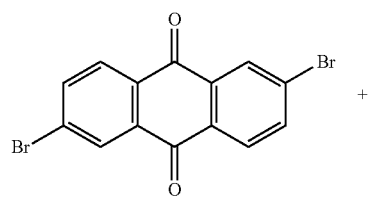

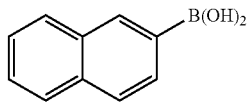

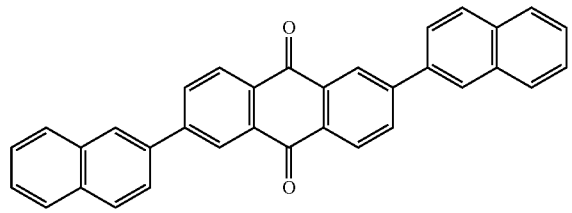

K2CO3 (29.1438 g, 0.21087 mol) was dissolved in distilled water (70 mL), and nitrogen gas was bubbled through the solution for 30 minutes. 2,6-dibromoanthraquinone) (7.5473 g, 20.69 mmol), 2-naphtyl boronic acid (10.0004 g, 58.15 mmol), tetrakis(triphenylphosphine)palladium(0) (Pd (pph3)4) (0.5772 g, 1.365 mmol), DME (240 mL), and THF (30 mL) were added to the mixture. The reaction mixture was refluxed for 20 hours and then cooled at room temperature, and the resultant solid compound was filtered under vacuum. The solid compound was washed with methanol and acetone, and then recrystallized, giving 2,6-bis(2-naphtyl)anthraquinone (6.19 g, 13.44 mmol, 65%).

3) Synthesis of 2,6-di(2-naphtyl)anthracene

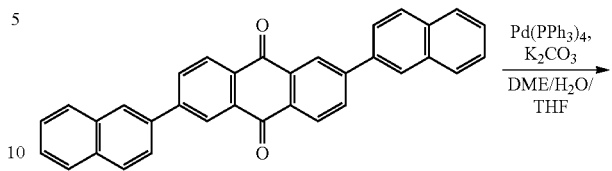

2,6-bis(2-naphtyl)anthraquinone) (6.19 g, 13.44 mmol), HI (50 mL), and H3PO2 (30 mL) were dissolved in glacial acetic acid (150 mL) under nitrogen gas, and refluxed at 1500 for 5 days. The reaction mixture solution was cooled at room temperature, and the resulting solid was separated by vacuum distillation and then washed with an excessive amount of distilled water and ethanol (EtOH). The resulting solid was recrystallized with CH2Cl2 and MeOH, thereby giving pure compound 3, i.e., 2,6-di(2-naphtyl)anthracene (2.6 g, 6.04 mmol, 45%).

4) Synthesis of 2,6-dibromo-9,10-di-iso-propylanthracen

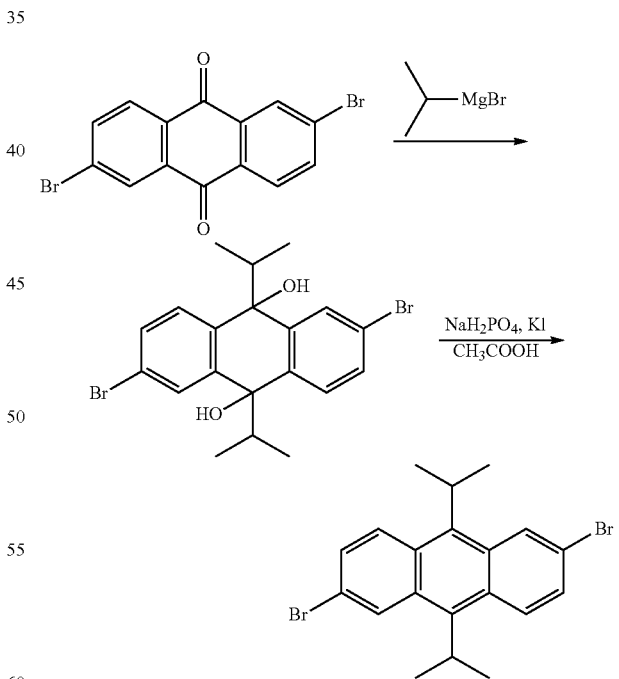

2,6-dibromoanthraquinone (15.762 g, 43.07 mmol) was dissolved in THF (300 mL) under nitrogen gas, and cooled at −78☐ using a dry ice-acetone bath. Iso-propyl magnesium bromide (2.9M sol. In 2-methyl THF, 30 mL, 87.00 mmol) was gradually added to the mixture at 780, and stirred for 1 hour. The temperature of the reaction container was raised to room temperature and stirred for 18 hours, and then an NH4Cl solution (50 mL) was added to the mixture in an ice bath. The reaction mixture was extracted with EtOAc (100 mL×3), and the organic layer was dehydrated with MgSO4. The reaction mixture was filtered in vacuum, and the solvent was removed. The mixture was subjected to silica column chromatography (Hexane), thus giving a pure compound (14.14 g, 31.13 mmol, 72%). The compound, KI (21.54 g, 129.76 mmol), and NaH2PO4.H2O (26.82 g, 194.36 mmol) were dissolved in acetic acid (300 mL) and refluxed for 17 hours. The reaction mixture was cooled at room temperature, and neutralized using a 6N NaOH aqueous solution. The organic layer was extracted with dichloromethane (100 mL×4), dried over MgSO4, and filtered in vacuum. After removing the solvent, the residue was separated by silica column chromatography (Hexane), thereby giving pure compound 5, i.e., 2,6-dibromo-9,10-di-iso-propylanthracene (8.64 g, 20.56 mmole, 66%).

5) Synthesis of 2-bromo-9,10-diisopropyl-6-(3,5-di-tert-butylphenyl)anthracene

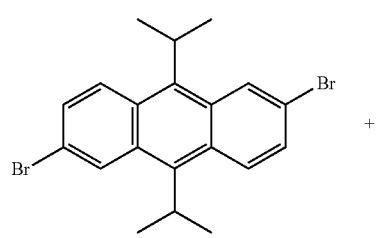

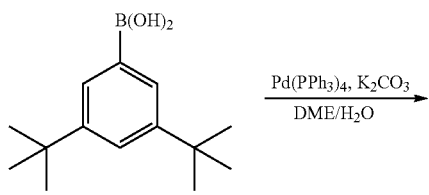

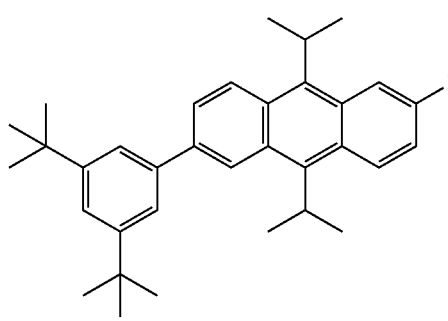

The same method as in Synthesis Example 3) was used on compound 5 (10.264 g, 24.43 mmol) and 3,5-di-tert-butylphenyl boronic acid (5.924 g, 25.30 mmol). The residue was separated by silica column chromatography (Hexane), thereby giving pure compound 6, i.e., 2-bromo-9,10-diisopropyl-6-(3,5-di-tert-butylphenyl)anthracene (7.28 g, 13.75 mmol, 56%).

6) Synthesis of 2-(dibenzothiophen-3-yl)-9,10-diisopropyl-6-(3,5-di-tert-butylphenyl)anthracene

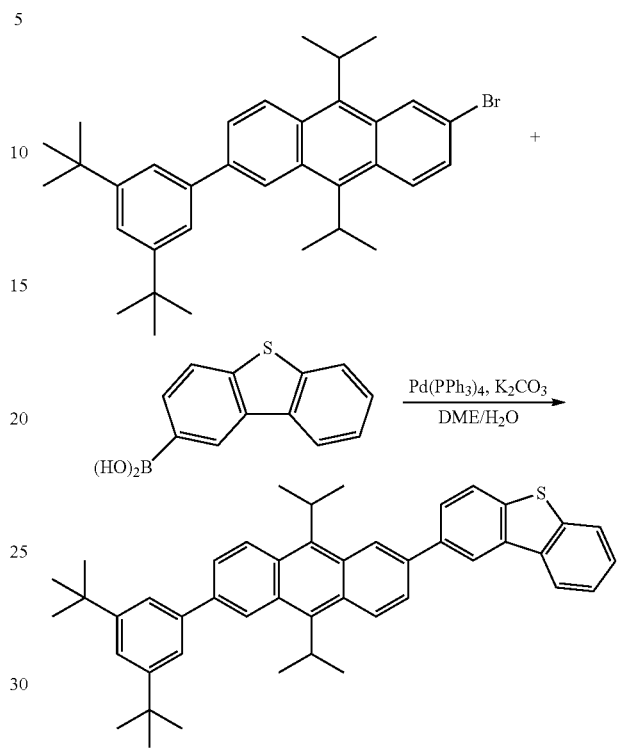

The same method as in Synthesis Example 5) was used on compound 6 (3.418 g, 6.45 mmol) and 2-dibenzothiphenyl boronic acid (1.682 g, 7.375 mmole). The residue was separated by silica column chromatography (Hexane), thereby giving pure compound 7, i.e., 2-(dibenzothiophen-3-yl)-9,10-diisopropyl-6-(3,5-di-tert-butylphenyl)anthracene (3.261 g, 5.152 mmol, 80%).

7) Synthesis of 2,8-dibromodibenzothiophene

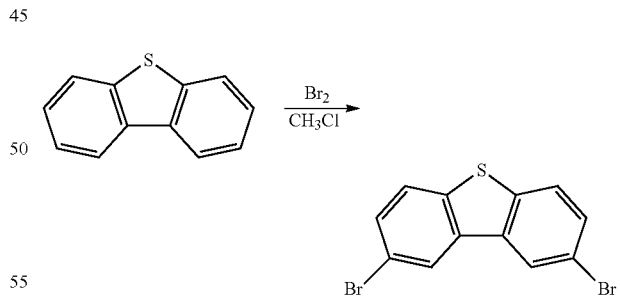

Dibenzothiophene (15.1552 g, 82.25 mmol) was dissolved in CHCl3 (150 mL), and Br2 (13.0 mL, 253.72 mmol) was gradually added to the mixture at 0° C. After 2 hours, the temperature of the reaction mixture was raised to room temperature, and stirred for 3 days. An excessive amount of MeOH was added to the mixture, and the mixture was stirred for 30 minutes, filtered in vacuum, and washed with an excessive amount of methanol, thereby white product 8, i.e., 2,8-dibromodibenzothiophene (22.87 g, 66.86 mmol, 81%).

8) Synthesis of 2-bromo-8-(3,5-di-tert-butylphenyl)dibenzothiophene

9) Synthesis of (8-(3,5-di-tert-butylphenyl)dibenzothiophen-2-yl)boronic acid

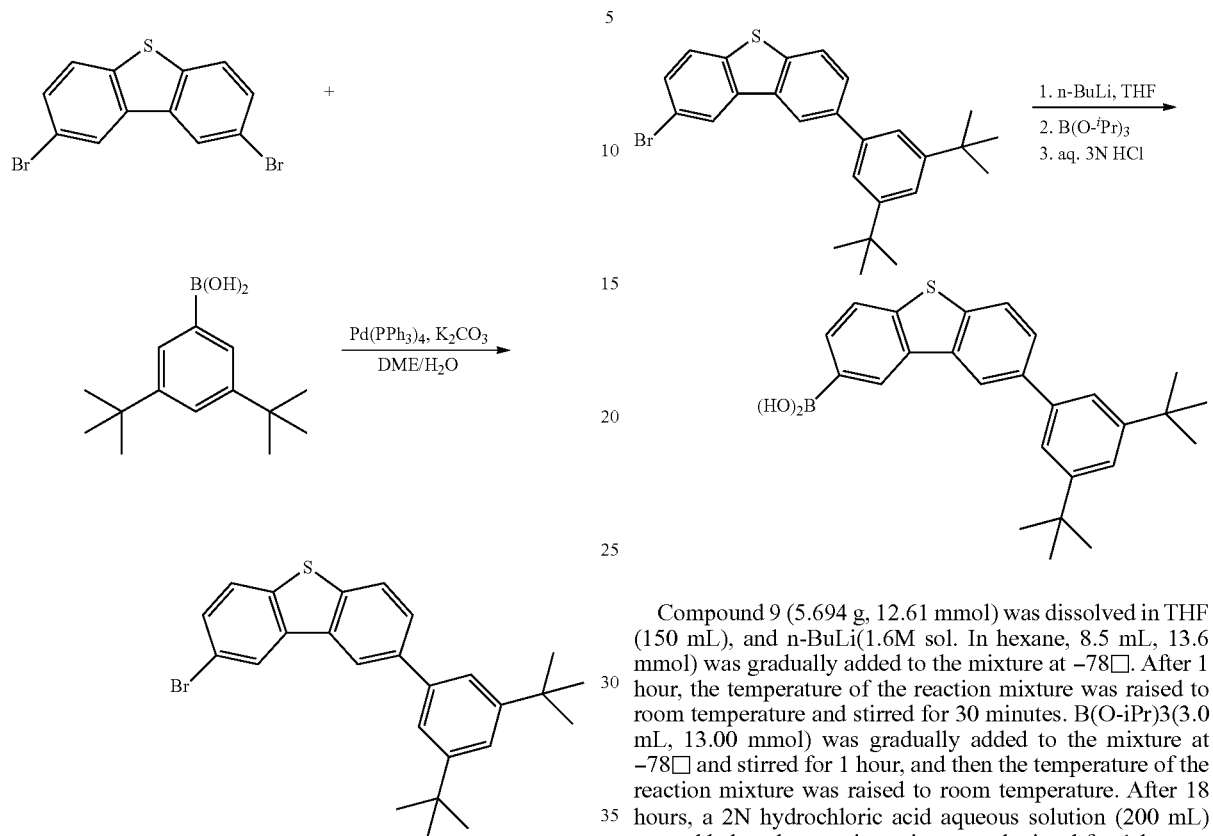

The same method as in Synthesis Example 5) was used on compound 8 (10.725 g, 31.35 mmol) and (3,5-di-tert-butylphenyl boronic acid) (7.942 g, 33.92 mmol), thereby giving pure compound 9, i.e., 2-bromo-8-(3,5-di-tert-butylphenyl) dibenzothiophene (6.421 g, 7.28 g, 14.24 mmol, 45%).

Compound 9 (5.694 g, 12.61 mmol) was dissolved in THF (150 mL), and n-BuLi(1.6M sol. In hexane, 8.5 mL, 13.6 mmol) was gradually added to the mixture at −78☐. After 1 hour, the temperature of the reaction mixture was raised to room temperature and stirred for 30 minutes. B(O-iPr)3(3.0 mL, 13.00 mmol) was gradually added to the mixture at −78☐ and stirred for 1 hour, and then the temperature of the reaction mixture was raised to room temperature. After 18 hours, a 2N hydrochloric acid aqueous solution (200 mL) was added to the reaction mixture and stirred for 1 hour at room temperature, and then the resulting white precipitate, i.e., 8-(3,5-di-tert-butylphenyl)dibenzothiophen-2-yl)boronic acid was separated by vacuum filtration. The white precipitate was immediately used the next reaction without an additional purification process.

10) Synthesis of 6-(3,5-di-tert-butylphenyl)-9,10-di-iso-propyl-2-(8-(3,5-di-tert-butylphenyl)dibenzothiophen-2-yl)anthracene

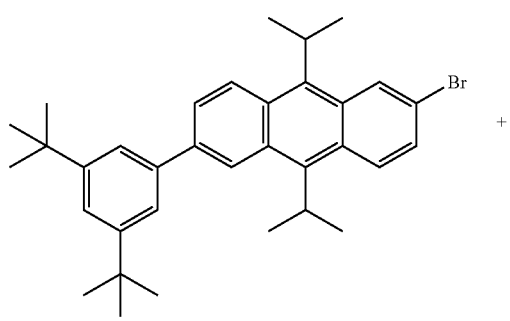

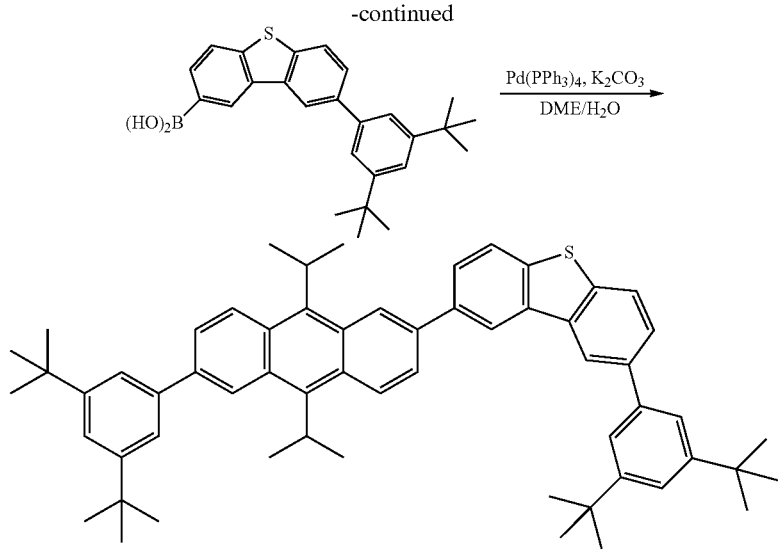

The same method as in Synthesis Example 5) was used on compound 6 (5.116 g, 9.66 mmol) and compound 10 (4.255 g, 10.22 mmol), thereby giving pure compound II, i.e., 6-(3,5-di-tert-butylphenyl)-9,10-di-iso-propyl-2-(8-(3,5-di-tert-butylphenyl)dibenzothiophen-2-yl)anthracene (5.004 g, 6.093 mmol, 63%).

Figure 4:
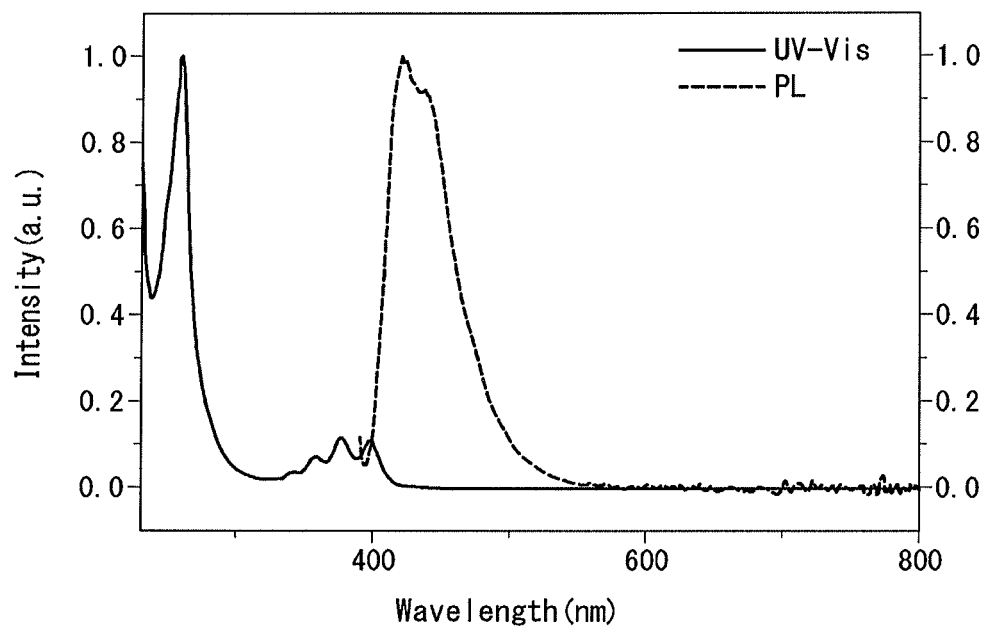
FIG. 4 is a graph showing measurements of the UV absorption spectrum and PL spectrum of compound 3 of the present invention.
Figure 5:
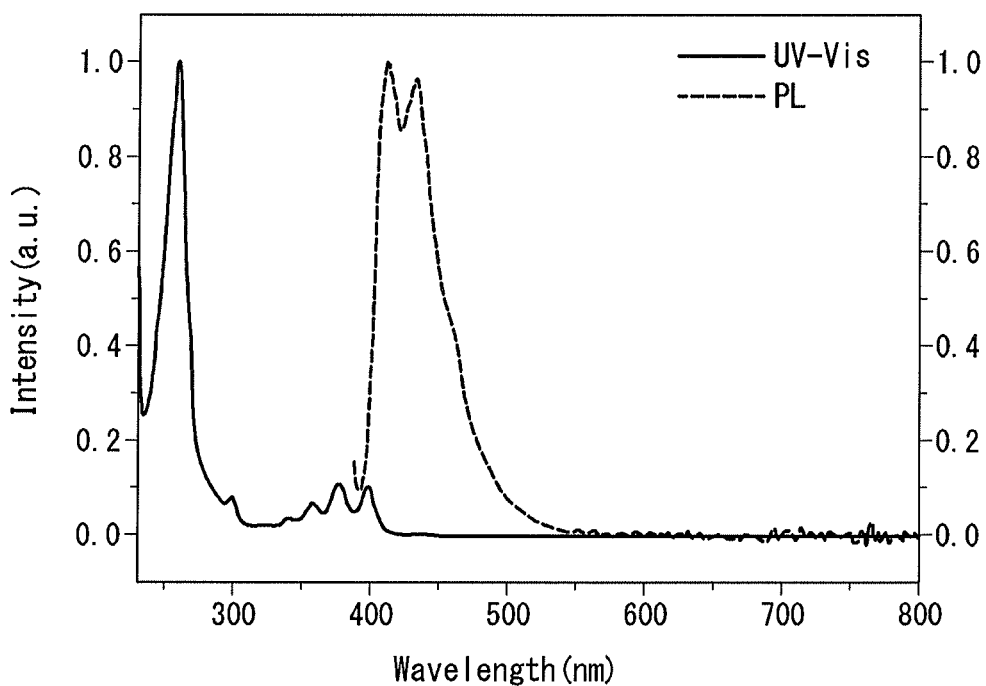
FIG. 5 is a graph showing measurements of the UV absorption spectrum and PL spectrum of compound 7 of the present invention.
Figure 6:
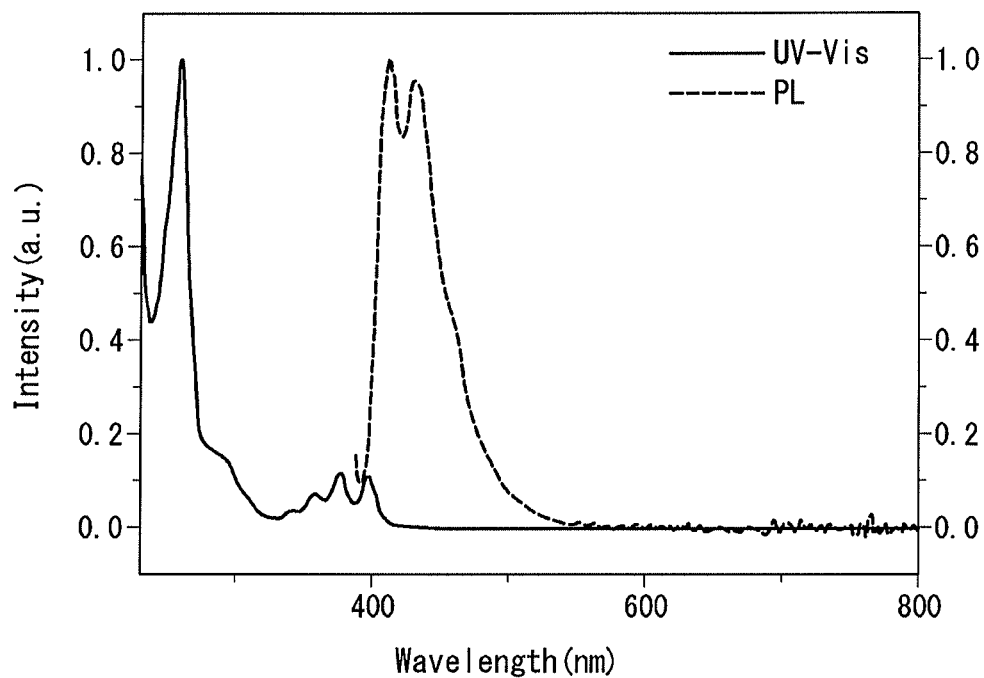
FIG. 6 is a graph showing measurements of the UV absorption spectrum and PL spectrum of compound II of the present invention.

FIGS. 4, 5, and 6 show measurements of the UV absorption spectra and PL spectra of the compounds 3, 7, and 11 produced in accordance with the aforementioned Synthesis Examples of the present invention. These measurements were listed in Table 1.

TABLE 1

| | Wavelength at peak level of UV absorption spectrum (nm) | Wavelength at peak level of PL spectrum (nm) | Energy bandgap |
|---|---|---|---|
| Compound 3 | 424 | 420,437 | 3.00 |
| Compound 7 | 410 | 411,432 | 3.02 |
| Compound 11 | 409 | 411,431 | 3.03 |

Referring to Table 1 and FIGS. 4 to 6, it was found out that the compounds 3, 7, and 11 produced in accordance with the exemplary embodiment of the present invention showed high energy band gap of 3.0 eV or greater. Accordingly, it was concluded that these compounds were suitable as blue fluorescent compounds.

Meanwhile, the following compounds A to G were designed by computer modeling according to the present invention. The computer program used was Spartan, and B3LYP and 6-31G* were used as the basis set.

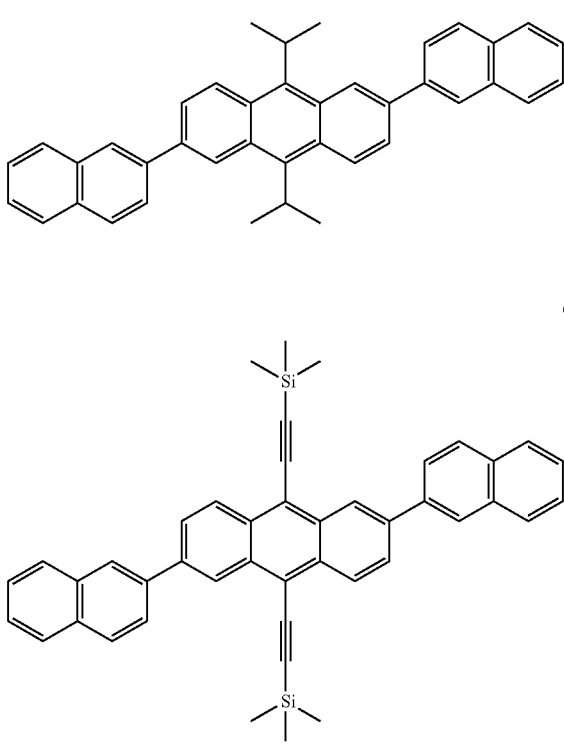

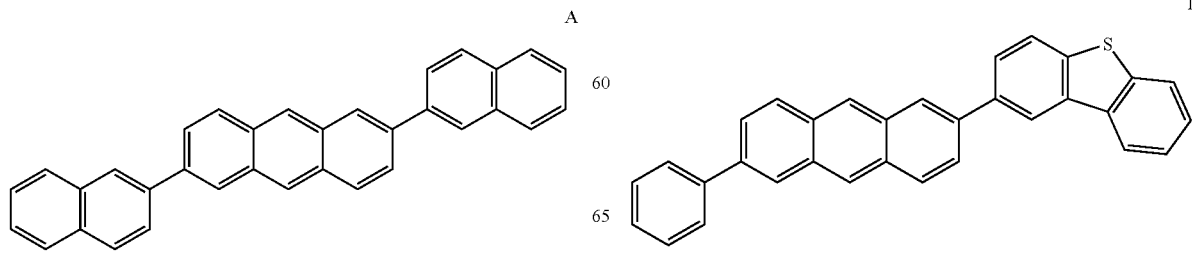

-continued

E

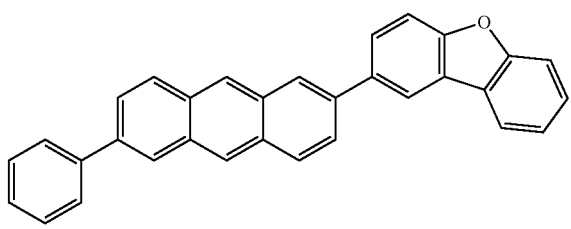

F

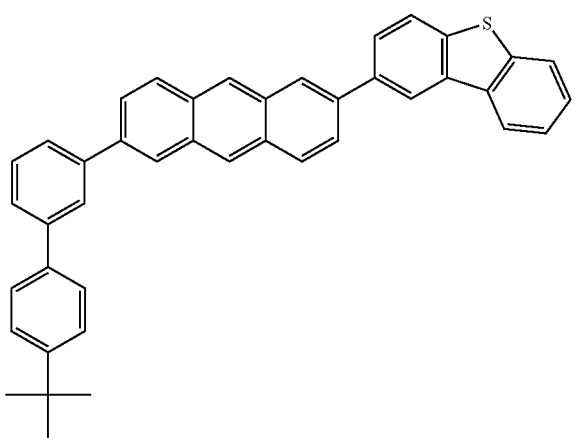

G

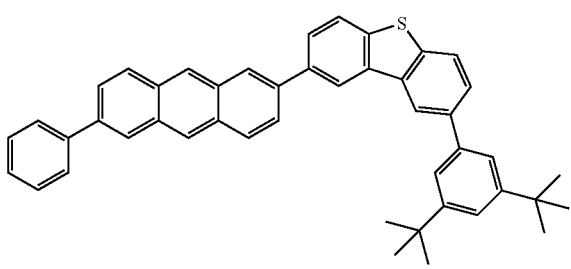

Figure 7:
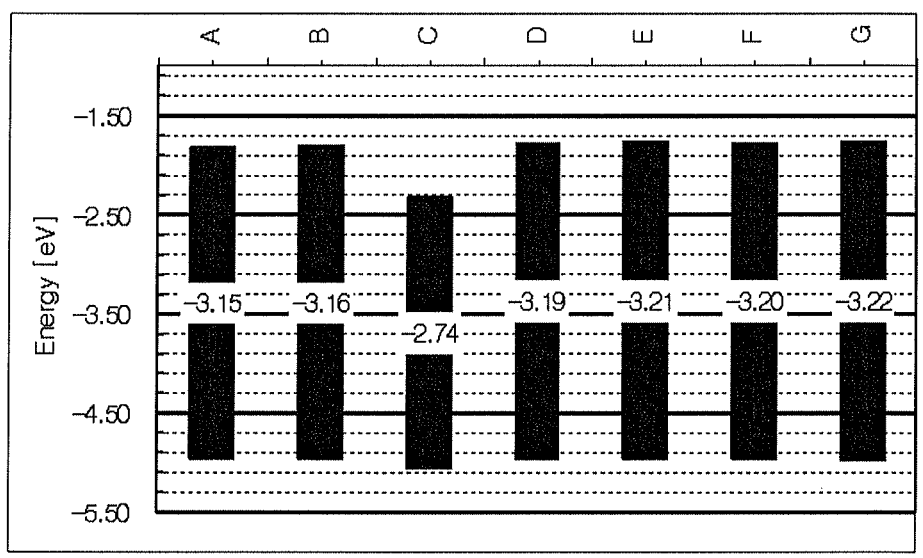
FIG. 7 is a graph showing measurements of the energy band gaps of compounds A to G of the present invention.

The energy band gaps of the designed compounds A to G were measured and shown in FIG. 7, and these measurements were listed in Table 2.

TABLE 2

| Compound | LUMO level (eV) | HOMO level (eV) | Energy band gap (eV) |
|---|---|---|---|
| A | −1.82 | −4.97 | −3.15 |
| B | −1.80 | −4.96 | −3.16 |
| C | −2.32 | −5.06 | −2.74 |
| D | −1.78 | −4.97 | −3.19 |
| E | −1.75 | −4.96 | −3.21 |
| F | −1.77 | −4.97 | −3.20 |
| G | −1.76 | −4.98 | −3.22 |

Referring to Table 2 and FIG. 2, a comparison of the compounds A, B, and C was made. The comparison result showed that, while the introduction of a saturated hydrocarbon chain to the 9 and 10 positions of anthracene led to no change in the energy levels of HOMO and LUMO, the introduction of substituents such as acetylene led to an increase in the conjugation length and resulted in a smaller energy band gap. Moreover, it was found out that, if various aromatic substituents (Phenyl, Naphtyl, Dibenzothiophenyl, Dibenzofuranyl, biphenyl, and phenyldibenzothiophenyl) are introduced to the 2 and 6 positions of anthracene, the LUMO energy levels was slightly increased and resulted in a slightly larger energy band gap.

As seen from above, even if the 9 and 10 positions of anthracene are substituted with saturated hydrocarbon derivatives, and various aromatic rings at the 2 and 7 positions are substituted with various saturated hydrocarbons, the energy band gaps showed large values of 3.2 eV or greater. Hence, it was concluded that the compounds used in the present invention were enough to be used as blue fluorescent compounds of organic light emitting diode devices.

The blue fluorescent compounds and the organic light emitting diode devices in accordance with the exemplary embodiment of the present invention have the advantage of improving outcoupling efficiency and device efficiency by forming the compounds to have horizontal orientation. Moreover, they have the advantage of increasing solubility in an organic solvent and making the solution process easy by substituting anthracene with saturated hydrocarbons.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:
1. A blue fluorescent compound represented by the following Chemical Formula 1:

[Chemical Formula 1]

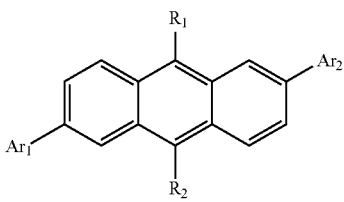

where $R_1$ and $R_2$ are each selected from the group consisting of H, $C_1$-$C_{18}$ saturated hydrocarbon carbons, branched saturated hydrocarbons, and saturated ring hydrocarbons, and $Ar_1$ is selected from the group consisting of $C_1$-$C_{20}$ aromatic compounds, heteroaromatic compounds, $C_1$-$C_{18}$ saturated hydrocarbons, $C_1$-$C_{18}$ branched saturated hydrocarbons, and $C_1$-$C_{18}$ saturated ring hydrocarbons; and $Ar_2$ is a heteroaromatic compound selected from the group consisting of:

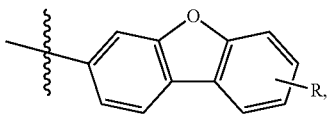

-continued

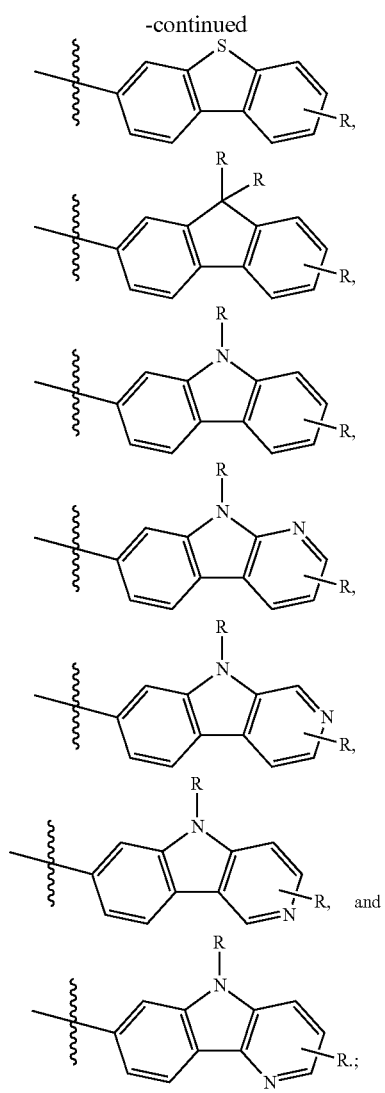

wherein R is H, methyl, ethyl, isopropyl, tertiary-butyl, n-butyl, 1,3,5-trimethylhexyl, or aryl.

2. The blue fluorescent compound of claim 1, wherein $R_1$ and $R_2$ are each selected from:

H, methyl, ethyl, isopropyl, tertiary-butyl, n-butyl, and 1,3,5-trimethylhexyl.

3. The blue fluorescent compound of claim 1, wherein $Ar_1$ is selected from the group consisting of:

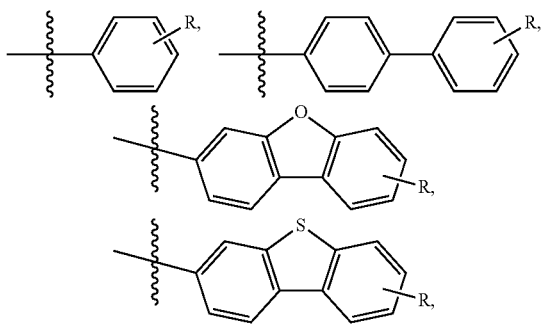

-continued

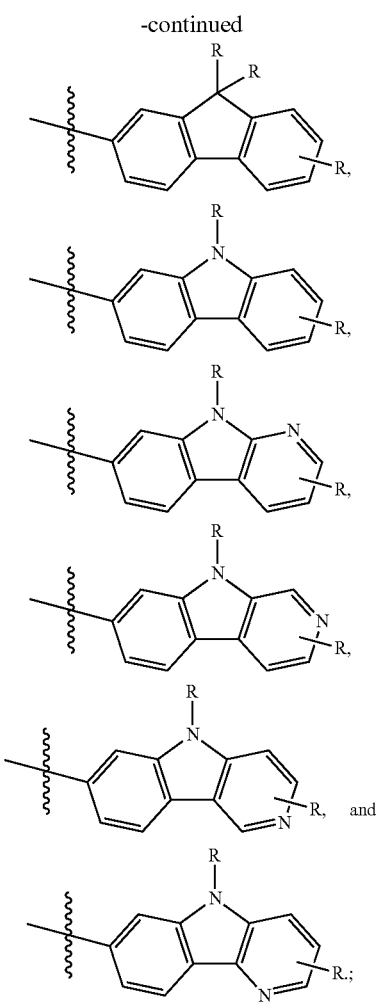

wherein R is wherein R is H, methyl, ethyl, isopropyl, tertiary-butyl, n-butyl, 1,3,5-trimethylhexyl, or aryl.

4. The blue fluorescent compound of claim 1, wherein the blue fluorescent compound is any one selected from the compounds represented below:

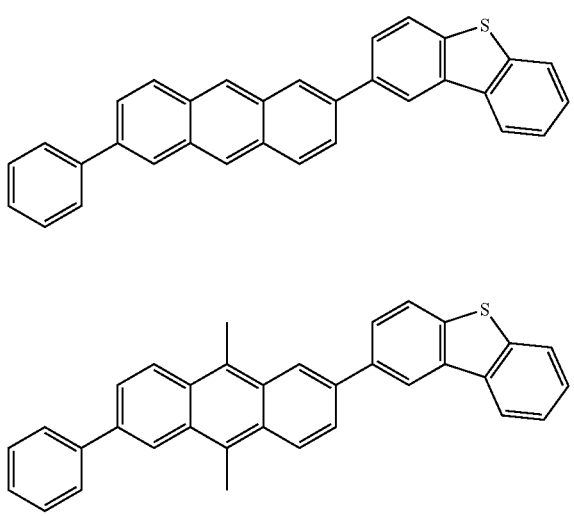

-continued
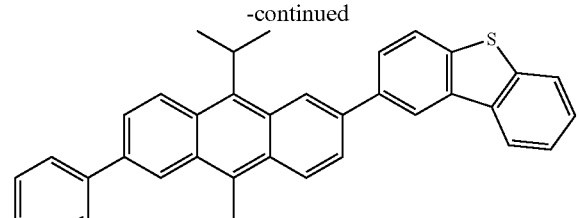
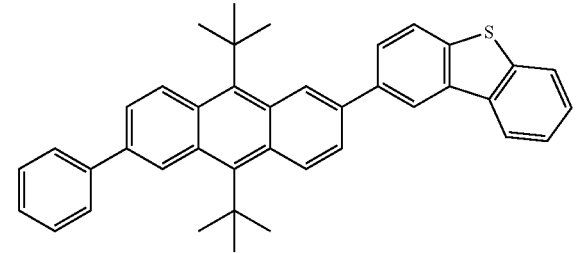
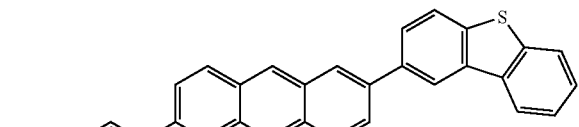
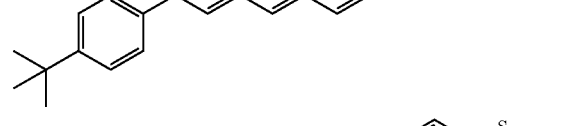
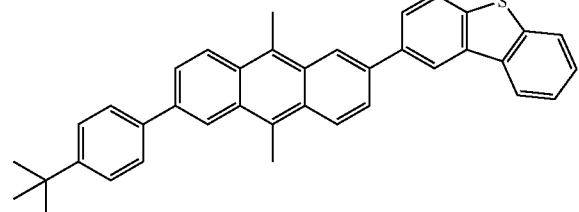
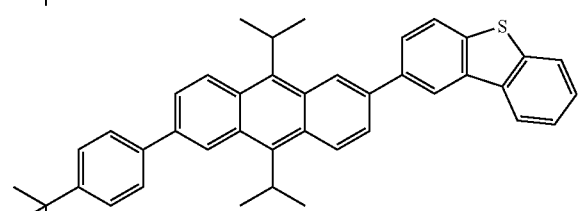
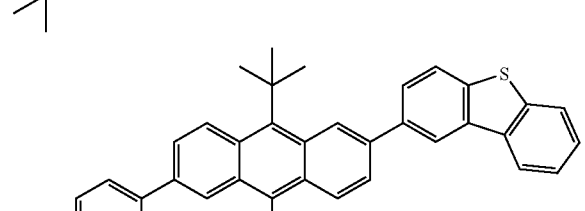
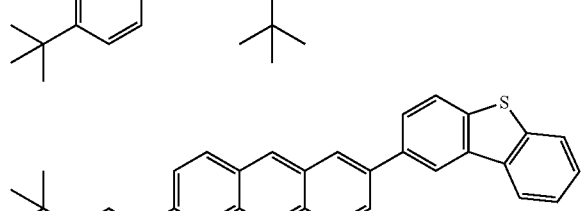
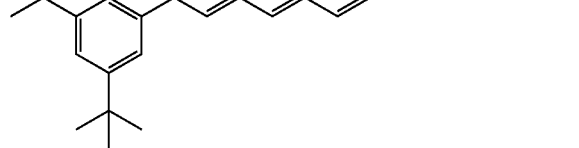
-continued
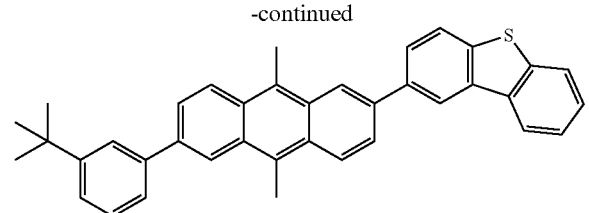
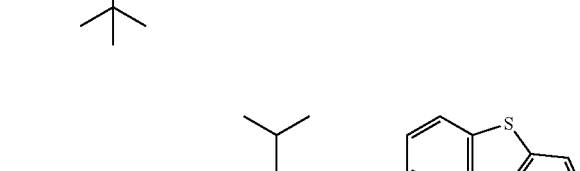
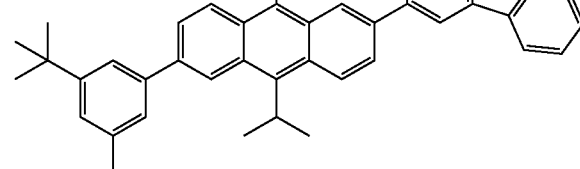
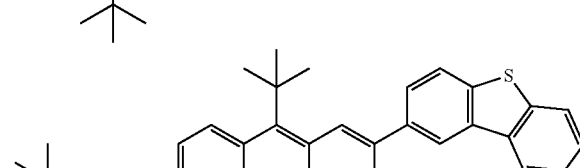
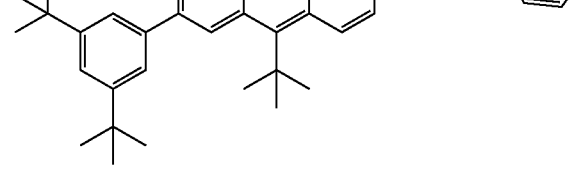
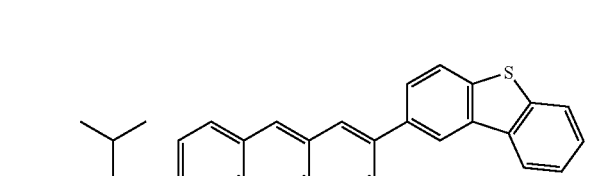
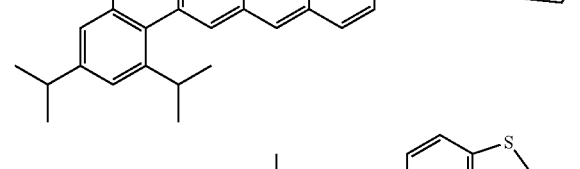
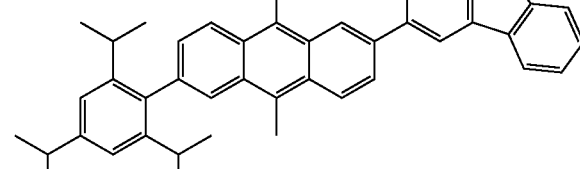
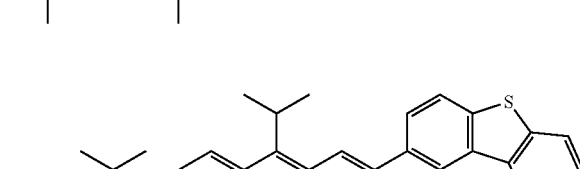
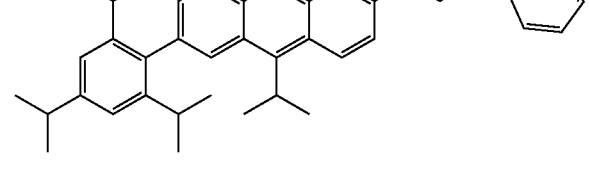

-continued
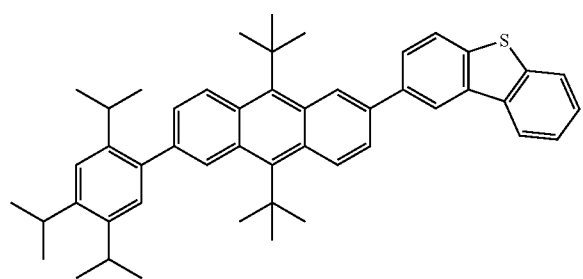
-continued
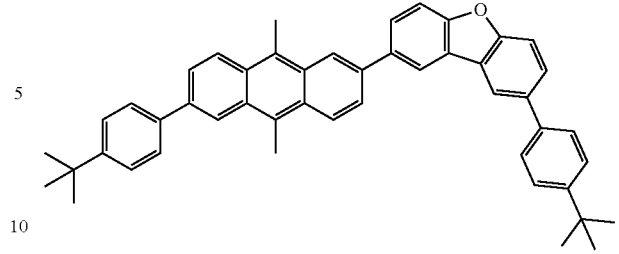

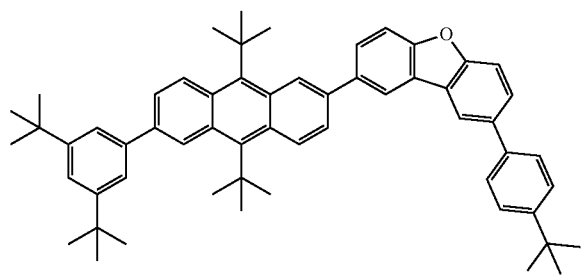
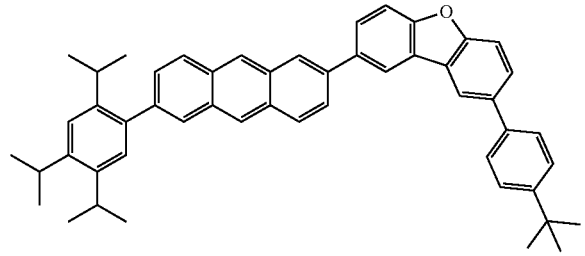
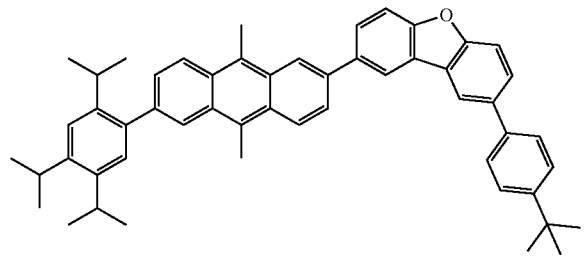
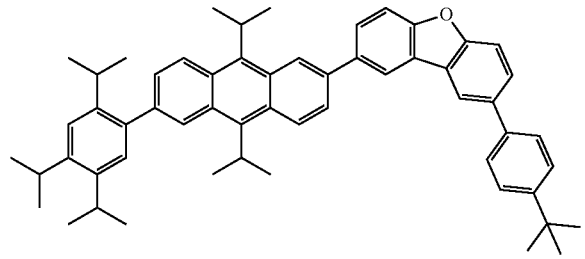
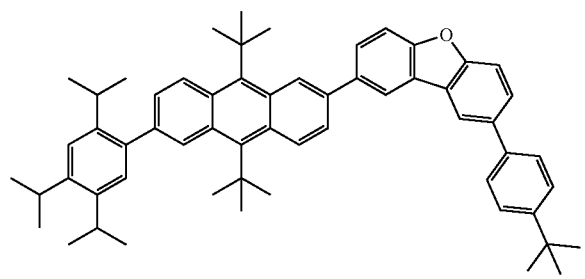
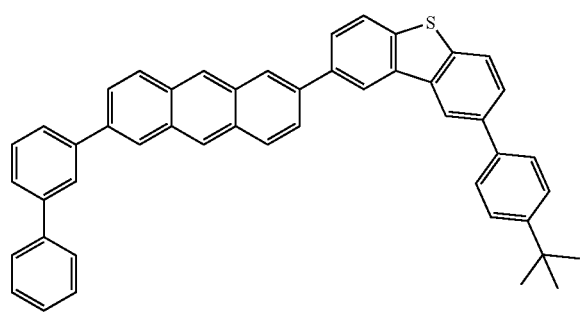
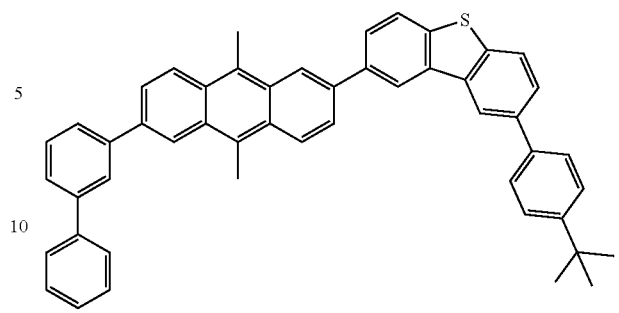
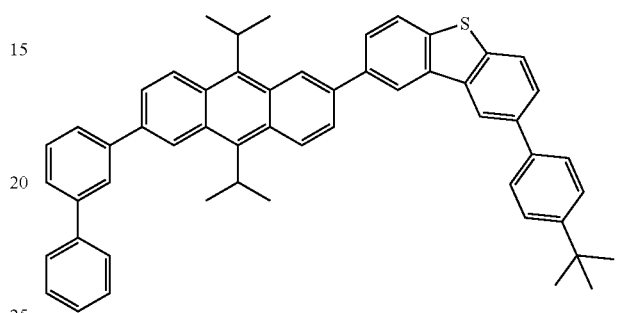
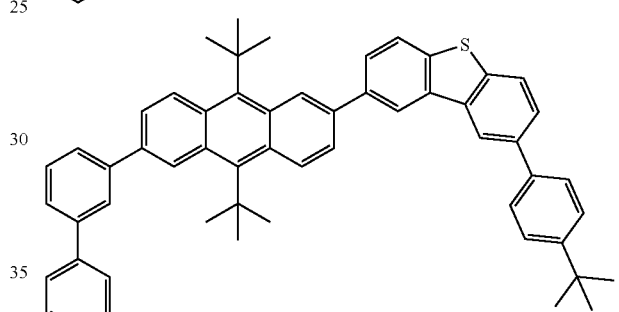
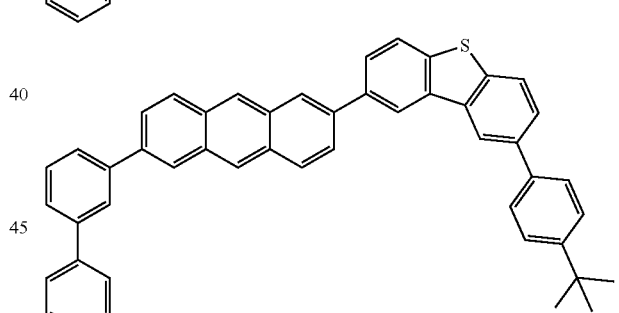
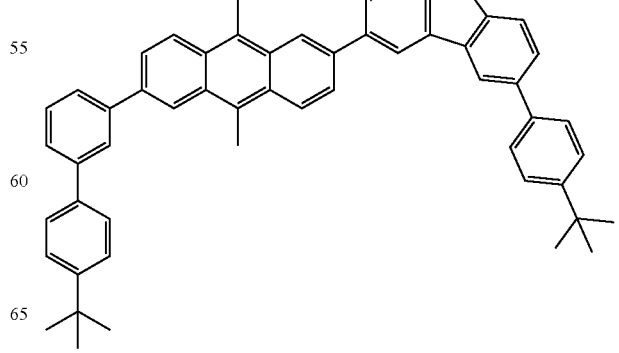

35
-continued
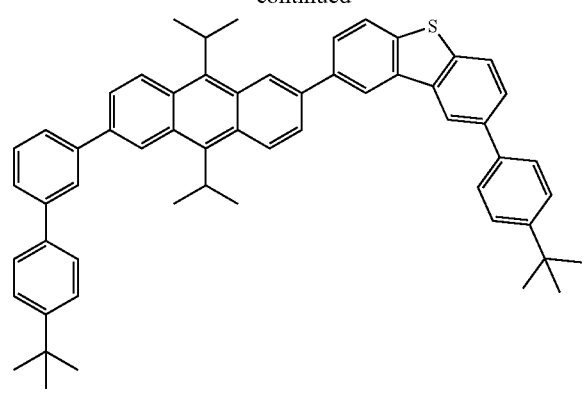
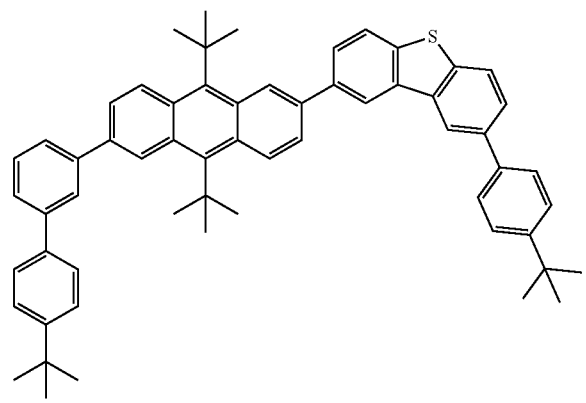
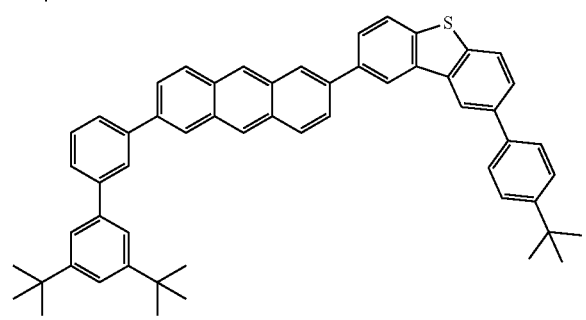
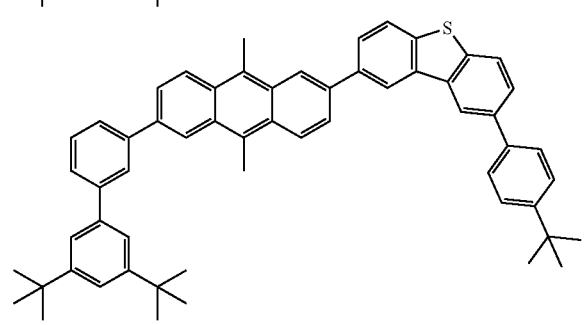
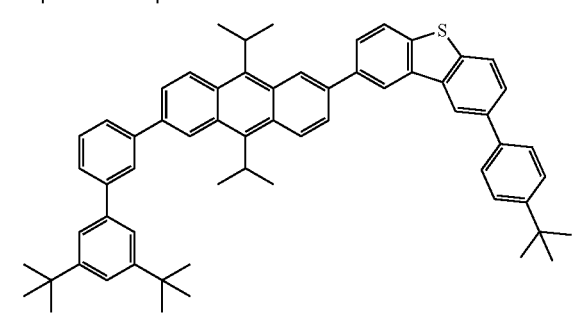
36
-continued
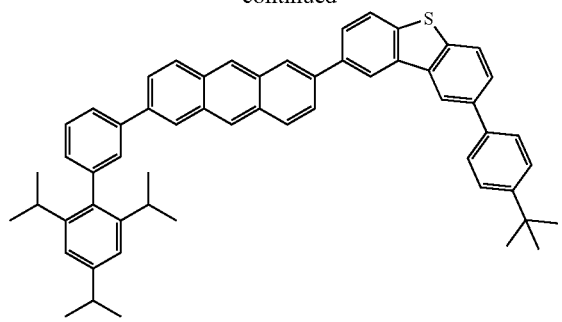
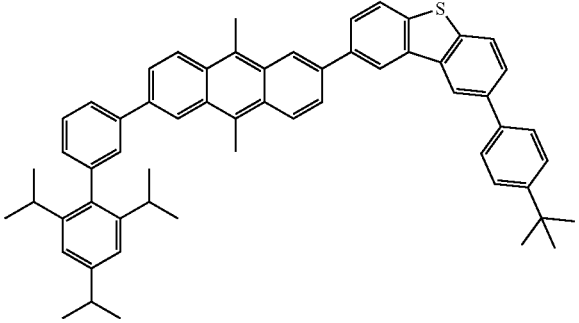
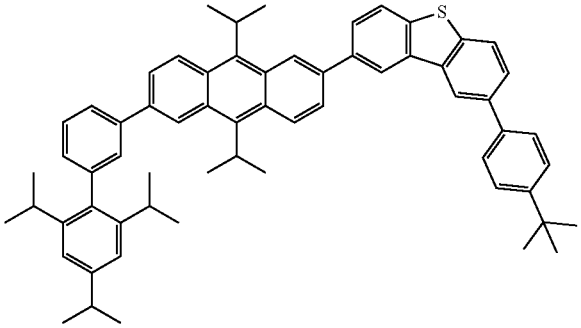
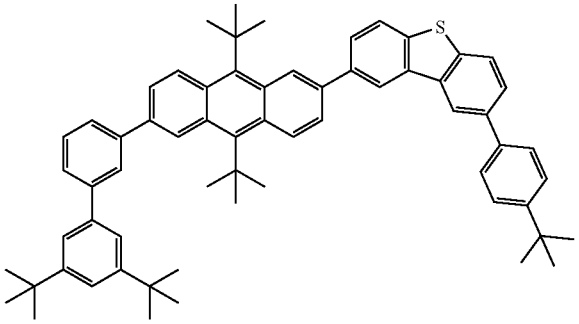
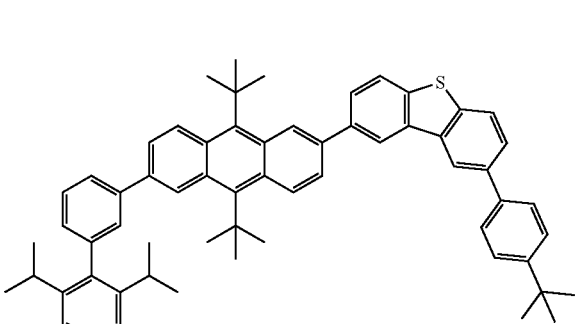

5. An organic light emitting diode device comprising an organic film formed between an anode and a cathode, the organic film comprising the blue fluorescent compound of claim 1.

6. The organic light emitting diode device of claim 5, wherein the organic film is an emission layer.

7. The organic light emitting diode device of claim 5, wherein the compound is used as the host of the emission layer.

8. The organic light emitting diode device of claim 5, further comprising one or more selected from the group consisting of a hole injection layer, a hole transport layer, an electron transport layer, and an electron injection layer between the anode and the cathode.

9. The blue fluorescent compound of claim 1, wherein $Ar_2$ is selected from:

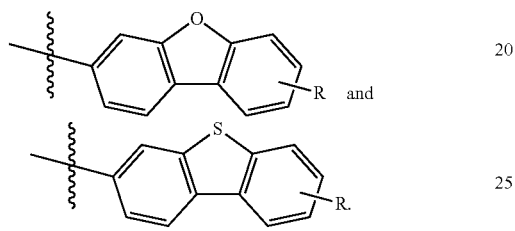

10. The blue fluorescent compound of claim 9, wherein the R substituent on $Ar_2$ is H or aryl.

* * * * *